(12) United States Patent
Jayaraman

(10) Patent No.: US 10,577,391 B2
(45) Date of Patent: *Mar. 3, 2020

(54) SELECTIVE PHOTOACTIVATION OF AMINO ACIDS FOR SINGLE STEP PEPTIDE COUPLING

(71) Applicant: VIBRANT HOLDINGS, LLC, San Carlos, CA (US)

(72) Inventor: Vasanth Jayaraman, San Mateo, CA (US)

(73) Assignee: Vibrant Holdings, LLC, San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/019,449

(22) Filed: Jun. 26, 2018

(65) Prior Publication Data
US 2019/0023734 A1  Jan. 24, 2019

Related U.S. Application Data

(63) Continuation of application No. 15/120,452, filed as application No. PCT/US2015/017173 on Feb. 23, 2015, now Pat. No. 10,040,818.

(60) Provisional application No. 61/942,903, filed on Feb. 21, 2014, provisional application No. 62/048,689, filed on Sep. 10, 2014.

(51) Int. Cl.
| | |
|---|---|
| C07K 1/04 | (2006.01) |
| C07K 1/08 | (2006.01) |
| C07D 257/04 | (2006.01) |
| C07K 1/06 | (2006.01) |
| C07K 1/10 | (2006.01) |

(52) U.S. Cl.
CPC ............ C07K 1/047 (2013.01); C07D 257/04 (2013.01); C07K 1/042 (2013.01); C07K 1/063 (2013.01); C07K 1/086 (2013.01); C07K 1/10 (2013.01)

(58) Field of Classification Search
CPC ........ C08F 2/48; C08F 2810/50; C08L 51/00; C08L 2201/02; C08L 83/10; H01L 2224/32225; H01L 21/0274; H01L 21/0271; H01L 25/50; H01L 51/422; G03F 7/0384
See application file for complete search history.

(56) References Cited

U.S. PATENT DOCUMENTS

| | | | | |
|---|---|---|---|---|
| 5,240,811 A | * | 8/1993 | Taylor | ............ C07D 257/04 430/270.1 |
| 9,216,399 B2 | | 12/2015 | Rajasekaran et al. | |
| 9,417,236 B2 | | 8/2016 | Rajasekaran et al. | |
| 10,006,909 B2 | | 6/2018 | Rajasekaran et al. | |
| 10,040,818 B2 | * | 8/2018 | Jayaraman | ............ C07K 1/047 |

FOREIGN PATENT DOCUMENTS

| | | |
|---|---|---|
| JP | 2005-264156 A | 9/2005 |
| WO | WO 1994/28075 A1 | 12/1994 |
| WO | WO 2014/052989 A2 | 4/1999 |
| WO | WO 99/41007 A2 | 8/1999 |
| WO | WO 1999/41007 A2 | 8/1999 |
| WO | WO 2008/097370 A2 | 8/2008 |
| WO | WO 2008/118167 A1 | 10/2008 |
| WO | WO 2012/154594 A1 | 11/2012 |
| WO | WO 2013/119845 A1 | 8/2013 |
| WO | WO 2014/078606 A2 | 5/2014 |

OTHER PUBLICATIONS

Alawode, O. E., et al., "Clean Photodecomposition of 1-methyl-4-phynyl-1H-tetrazole-5(4H)-thiones to Carbodiimides Proceeds via a Biradical," The Journal of Organic Chemistry, Jan. 7, 2011, vol. 76, No. 1, pp. 216-222.
Australian First Examination Report, Australian Application No. 174812, dated Mar. 18, 2017, 3 pages.
Canadian Office Action, Canadian Application No. 2,940,177, dated Jun. 28, 2017, 4 pages.
European Extended Search Report, European Application No. 15751793.9, dated Sep. 1, 2017, 7 pages.
Gundugola, A. S. V., "Syntheses, Photochemistry, and DNA Photocleavage of Compounds Containing Tetrazolethione Scaffolds," [online] Kansas State University, An Abstract of a Dissertation, 2011 [retrieved on Jan. 5, 2015], retrieved from the Internet<URL: http://krex.kstate.edu/dspace/handle/2097/12022>, 2 pages.
New Zealand First Examination Report, New Zealand Application No. 724210, dated Feb. 23, 2017, 3 pages.
New Zealand Second Examination Report, New Zealand Application No. 724210, dated Jun. 20, 2017, 2 pages.
PCT International Search Report and Written Opinion, PCT/US2015/017173, dated Jun. 3, 2015, 16 Pages.

(Continued)

*Primary Examiner* — Soren Harward
*Assistant Examiner* — Jia-Hai Lee
(74) *Attorney, Agent, or Firm* — Goodwin Procter LLP

(57) ABSTRACT

Disclosed herein are formulations, substrates, and arrays for amino acid and peptide synthesis on microarrays. In certain embodiments, methods for manufacturing and using the formulations, substrates, and arrays including one-step coupling, e.g., for synthesis of peptides in a C→N orientation are disclosed. In some embodiments, disclosed herein are formulations and methods for high efficiency coupling of biomolecules to a substrate.

14 Claims, 12 Drawing Sheets

Specification includes a Sequence Listing.

(56) References Cited

OTHER PUBLICATIONS

European Patent Office, Communication Pursuant to Article 94(3) EPC, EP Patent Application No. 15751793.9, dated Jul. 31, 2018, four pages.
United States Office Action, U.S. Appl. No. 15/120,452, dated Sep. 18, 2017, 14 pages.
Arimitsu K et al., "Development of Highly Sensitive Photoreactive Materials Utilizig Photobase-generating Reactions and Base Proliferation Reactions", Journal of Synthetic Organic Chemistry Japan, Jan. 1, 2012, pp. 508-516, vol. 70(5), Yuki Gosei Kagaku Kaokai, Tokyo, JP (with English Abstract).
Camarero, J., "Recent Developments in the Site-Specific Immobilization of Proteins Onto Solid Supports," Biopolymers, 2008, pp. 450-458, vol. 90, No. 3.
Chen, "Solid-Phase Peptide Synthesis (SPPS) and Applications of Synthetic Peptides," Proteomics 2010.
Han, S-Y. et al., "Recent Development of Peptide Coupling Reagents in Organic Synthesis," Tetrahedron, 2004, pp. 2447-2467, vol. 60.
Lin et al., "Synthesis of Water Soluble Photoinitiators of Thioxanthone Derivatives III" Huadong Ligong Daxue Xuebao, Journal of East China University of Science and Technology, 2000, pp. 212-214, 220, vol. 26, No. 2 (with English abstract).
Suyama K. et al., "Photobase Generators: RecentProgress and Application Trend in Polymer Systems", Progress in Polymer Science, Feb. 1, 2009, pp. 194-209, vol. 34(2), Pergamon Press, Oxford, GB.
Tapia, V. et al., "Evaluating the Coupling Efficiency of Phosphorylated Amino Acids for SPOT Synthesis," J. Peptide Sci., 2008, pp. 1309-1314, vol. 14, No. 12.

\* cited by examiner

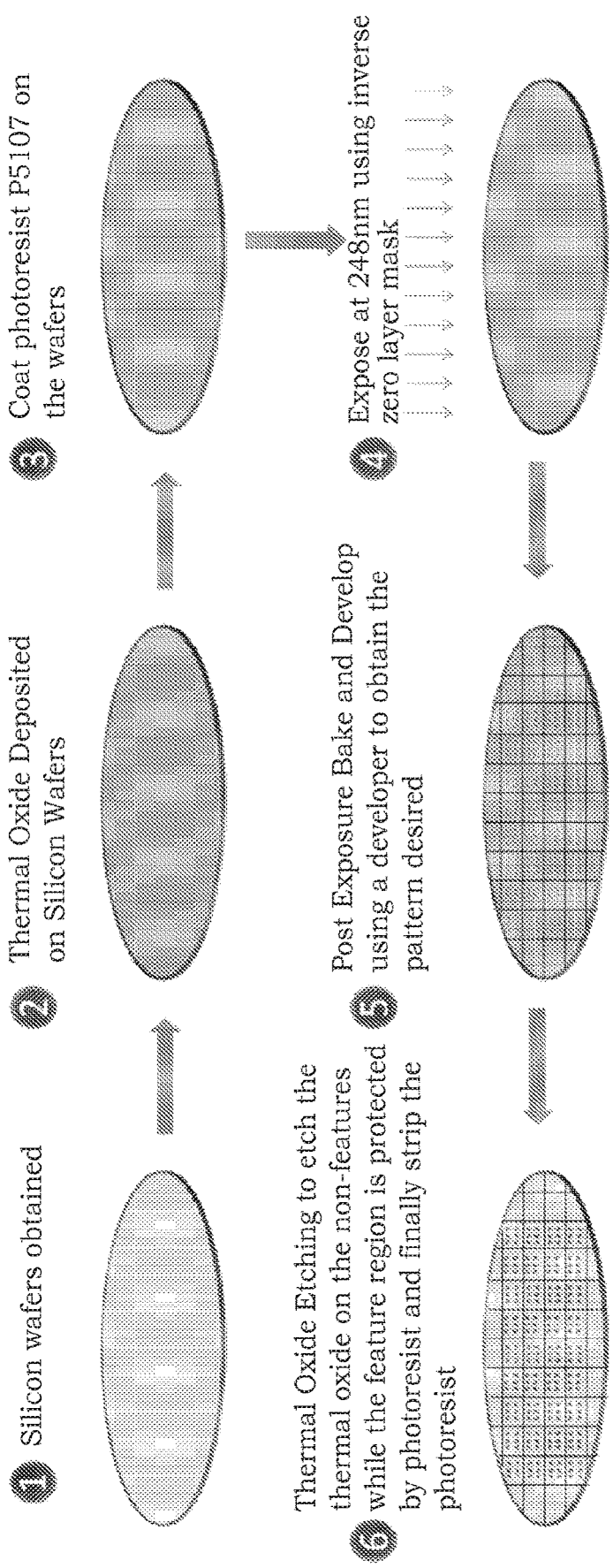
FIG. 1A: Wafer Substrate Preparation

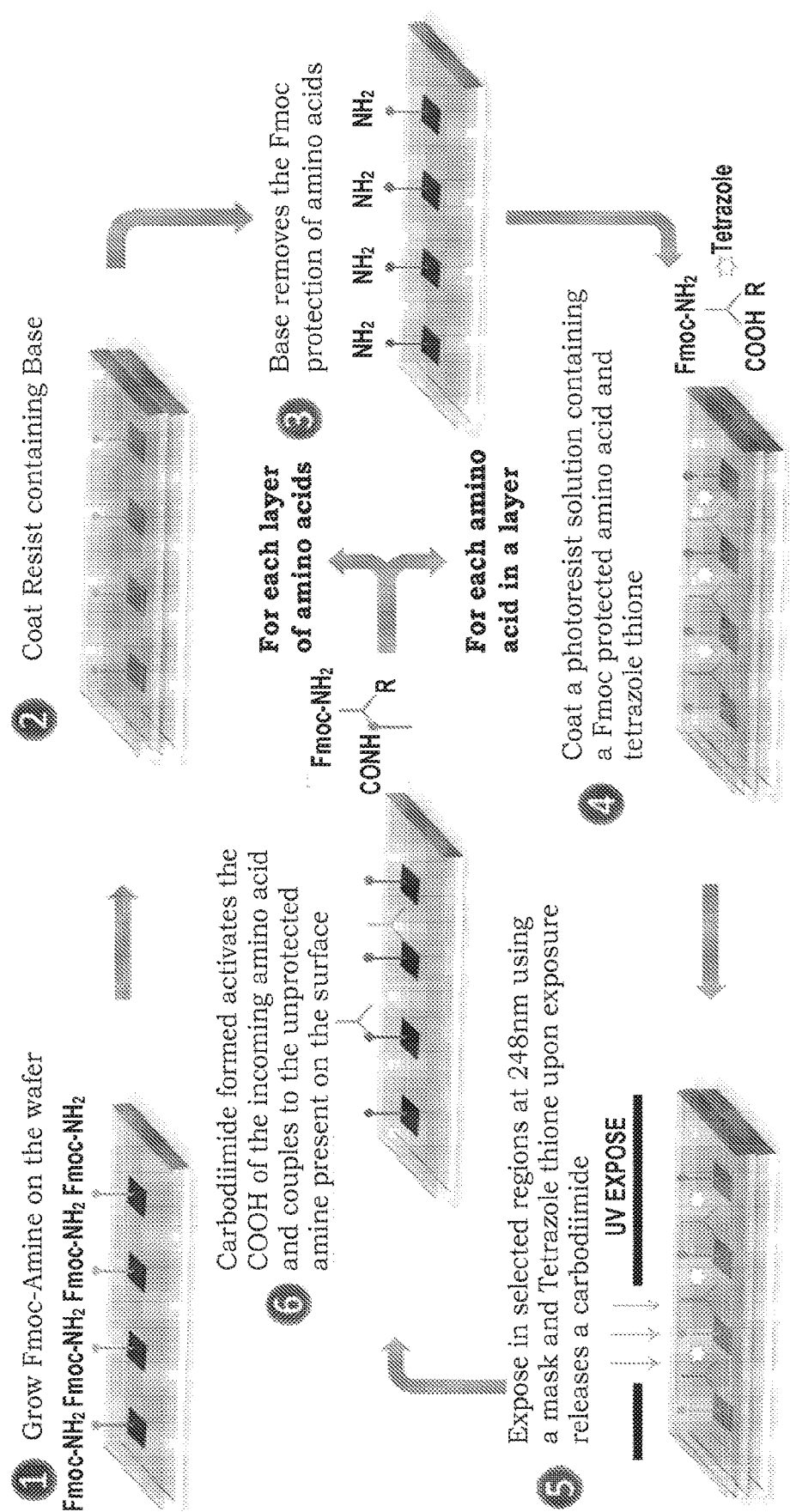
FIG. 2: Peptide Array Synthesis

SELECTIVE PHOTOACTIVATION OF AMINO ACIDS FOR SINGLE STEP PEPTIDE COUPLING

CROSS-REFERENCE TO RELATED APPLICATIONS

This application is a continuation of U.S. application Ser. No. 15/120,452, filed on Aug. 19, 2016, which is a national stage entry under 35 U.S.C. § 371 of International Application No. PCT/US2015/017173, filed Feb. 23, 2015, which claims the benefit of U.S. Provisional Patent Application No. 61/942,903 filed Feb. 21, 2014, and U.S. Provisional Patent Application No. 62/048,689, filed Sep. 10, 2014, the disclosures of which are incorporated by reference in their entirety for all purposes.

SEQUENCE LISTING

This application contains a Sequence Listing which has been filed electronically in ASCII format and is hereby incorporated by reference in its entirety. Said ASCII copy, created on Jun. 11, 2017, is named 28900US CRF Sequence-Listing.txt and is 3,249 bytes in size.

BACKGROUND

A typical microarray system is generally comprised of biomolecular probes, such as DNA, proteins, or peptides, formatted on a solid planar surface like glass, plastic, or silicon chip, plus the instruments needed to handle samples (automated robotics), to read the reporter molecules (scanners) and analyze the data (bioinformatic tools). Microarray technology can facilitate monitoring of many probes per square centimeter. Advantages of using multiple probes include, but are not limited to, speed, adaptability, comprehensiveness and the relatively cheaper cost of high volume manufacturing. The uses of such an array include, but are not limited to, diagnostic microbiology, including the detection and identification of pathogens, investigation of anti-microbial resistance, epidemiological strain typing, investigation of oncogenes, analysis of microbial infections using host genomic expression, and polymorphism profiles.

Recent advances in genomics have culminated in sequencing of entire genomes of several organisms, including humans. Genomics alone, however, cannot provide a complete understanding of cellular processes that are involved in disease, development, and other biological phenomena; because such processes are often directly mediated by polypeptides often as participants in ligand-receptor binding reactions. Given the large numbers of polypeptides are encoded by the genome of an organism, the development of high throughput technologies for analyzing polypeptides is of paramount importance.

Peptide arrays with distinct analyte-detecting regions or probes can be assembled on a single substrate by techniques well known to one skilled in the art. A variety of methods are available for creating a peptide microarray. These methods include: (a) chemo selective immobilization methods; and (b) in situ parallel synthesis methods which can be further divided into (1) SPOT synthesis and (2) photolithographic synthesis. However, chemo selective immobilization methods of the prior art tend to be cumbersome, requiring multiple steps, or are difficult to control spatially, limiting the feature density that can be achieved using these methods, and in situ parallel synthesis methods of the prior art suffer from deficiencies relating to low or inconsistent coupling efficiencies across multiple coupling cycles. The methods in the prior art suffer from slow feature synthesis. The present invention addresses these and other shortcomings of the prior art by providing substrates, systems, and methods for array synthesis and biomolecular analysis as described in detail below.

SUMMARY

Embodiments of the invention include formulations, substrates, and arrays. Embodiments also include methods for manufacturing and using the formulations, substrates, and arrays. One embodiment includes an array that is manufactured using a photoactive coupling formulation, a carboxylic acid activating compound, and a substrate comprising carboxylic acid groups. In some embodiments, the photoactive coupling formulation comprises a photoactive compound, a coupling molecule, a polymer, and a solvent. Another embodiment includes an array that is manufactured using a coupling formulation, a photoactive carboxylic acid activating compound, and a substrate comprising carboxylic acid groups. In some embodiments, the coupling formulation comprises a coupling molecule, a polymer, and a solvent. In some embodiments, attaching the coupling molecule to the substrate comprises selectively exposing either the photoactive compound or the photoactive carboxylic acid activating compound to light. In some embodiments, the photoactive compound is about 0.5-5% by weight of the total formulation.

Examples of coupling molecules include, but are not limited, to amino acids, peptides, proteins, DNA binding sequences, antibodies, oligonucleotides, nucleic acids, peptide nucleic acids ("PNA"), deoxyribonucleic acids (DNA), ribonucleic acids (RNA), peptide mimetics, nucleotide mimetics, chelates, biomarkers and the like. In one embodiment, the coupling molecule comprises a naturally occurring or artificial amino acid or polypeptide. In some embodiments, the artificial amino acid is a D-amino acid. In some embodiments, the coupling molecule is 1-2% by weight of the total formulation. In some embodiments, the coupling molecule comprises a protected group. In some embodiments, the group is protected by Fmoc.

In some embodiments, the photoactive carboxylic acid activating compound comprises a carbodiimide precursor compound of formula (I):

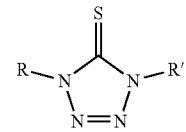

wherein
R is selected from a group comprising substituted or unsubstituted alkyl, and R further comprises a water-solubilizing group; and
R' is substituted or unsubstituted aryl.

Particular embodiments of photobase generator compounds and carbodiimide precursor compounds are shown in Table 1.

In certain embodiments, the carboxylic acid activating compound, also referred to as a "coupling reagent" herein, is a carbodiimide. In some embodiments, the polymer is polymethyl methacrylate.

In some embodiments, the formulations are miscible with water. In some embodiments, the solvent is water, an organic solvent, or a combination thereof. In certain embodiments, the organic solvent comprises ethyl lactate or methylpyrrolidone. In some embodiments, the solvent is about 80-90% by weight of the total formulation.

Also encompassed is a substrate, comprising: a first layer, wherein the layer comprises a plurality of unprotected amino groups. In some embodiments, the first layer is a porous layer. In some embodiments, the amino groups are oriented in multiple directions on the surface of the porous layer.

In an embodiment, the first layer is coupled to a support layer. In an embodiment, the first layer is coupled to a silicon wafer. In certain embodiments, the porous layer comprises dextran. In other embodiments, the porous layer comprises porous silica. In an embodiment, the porous layer comprises pores of a pore size of about 2 nm to 100 μm. In an embodiment, the porous layer comprises a porosity of about 10-80%. In an embodiment, the porous layer comprises a thickness of about 0.01 μm to about 10,000 μm.

In an embodiment, the substrate further comprises a plurality of pillars operatively coupled to the planar layer in positionally-defined locations, wherein each pillar has a planar surface extended from the planar layer, wherein the distance between the surface of each pillar and the upper surface of the layer is between 1,000-5,000 angstroms, and wherein the plurality of pillars are present at a density of greater than 10,000/cm$^2$, and wherein the first layer is deposited on the planar surface of the pillars. In some embodiments, the surface area of each pillar surface is at least 1 μm$^2$. In some embodiments, the surface area of each pillar surface has a total area of less than 10,000 μm$^2$. In some embodiments, the distance between the surface of each pillar and the lower surface of the layer is 2,000-7,000 angstroms. In some embodiments, the planar layer is 1,000-2,000 angstroms thick. In some embodiments, the center of each pillar is at least 2,000 angstroms from the center of any other pillar. In some embodiments, the surface of each pillar is parallel to the upper surface of the planar layer. In some embodiments, the surface of each pillar is substantially parallel to the upper surface of the planar layer. In some embodiments, each pillar comprises silicon dioxide or silicon nitride. In some embodiments, each pillar is at least 98-99% silicon dioxide by weight.

In an embodiment, the substrate further comprises a linker molecule having a free amino terminus attached to at least one of the carboxylic acid groups. In some embodiments, the substrate further comprises a linker molecule having a free carboxylic acid group attached to at least one of the carboxylic acid groups. In some embodiments, the substrate further comprises a coupling molecule attached to at least one of the carboxylic acid groups. In some embodiments, the substrate further comprises a polymer chain attached to at least one of the carboxylic acid groups.

In an embodiment, the polymer chain comprises a peptide chain. In some embodiments, the polymer chain is attached to at least one of the carboxylic acid groups via a covalent bond.

Another embodiment encompasses a three-dimensional array of features attached to a surface at positionally-defined locations, the features each comprising: a collection of peptide chains of determinable sequence and intended length, wherein within an individual feature, the fraction of peptide chains within the collection having the intended length is characterized by an average coupling efficiency for each coupling step of at least 98%.

In an embodiment, the array comprises a porous layer. In some embodiments, the porous layer comprises a plurality of free carboxylic acid groups. In some embodiments, the porous layer comprises a plurality of coupling molecules each attached to the array via a carboxylic acid group. In some embodiments, the porous layer comprises a plurality of peptide chains each attached to the array via a carboxylic acid group.

In certain embodiments, the average coupling efficiency of each coupling step is at least 98.5%. In some embodiments, the average coupling efficiency of each coupling step is at least 92%, 93%, 94%, 95%, 96%, 97%, 98%, or 99%. In some embodiments, each peptide chain is from 6 to 60 amino acids in length. In some embodiments, each peptide chain is at least 6 amino acids in length. In some embodiments, each peptide chain is at least 6, 10, 15, 20, 25, 30, 35, 40, 45, 50, 55, or 60 amino acids in length. In some embodiments, each peptide chain comprises one or more L amino acids. In some embodiments, each peptide chain comprises one or more D amino acids. In some embodiments, each peptide chain comprises one or more naturally occurring amino acids. In some embodiments, each peptide chain comprises one or more synthetic amino acids. In some embodiments, the array comprises at least 1,000 different peptide chains attached to the surface. In some embodiments, the array comprises at least 10,000 different peptide chains attached to the surface.

In an embodiment, each of the positionally-defined locations is at a different, known location that is physically separated from each of the other positionally-defined locations. In some embodiments, each of the positionally-defined locations comprises a plurality of identical sequences. In some embodiments, each positionally-defined location comprises a plurality of identical sequences unique from the other positionally-defined locations. In some embodiments, each of the positionally-defined locations is a positionally-distinguishable location. In certain embodiments, each determinable sequence is a known sequence. In certain embodiments, each determinable sequence is a distinct sequence. In some embodiments, the features are covalently attached to the surface. In some embodiments, peptide chains are attached to the surface through a linker molecule or a coupling molecule.

In certain embodiments, the features comprise a plurality of distinct, nested, overlapping peptide chains comprising subsequences derived from a source protein having a known sequence. In an embodiment, each peptide chain in the plurality is at least 5 amino acids in length. In some embodiments, each peptide chain in the plurality is at least 5, 10, 15, 20, 25, 30, 35, 40, 45, 50, 55, or 60 amino acids in length.

In some embodiments, the features comprise a plurality of peptide chains each having a random, determinable sequence of amino acids.

One embodiment includes a method of attaching a coupling molecule to a substrate, comprising: obtaining a substrate comprising a plurality of carboxylic acid groups for linking to a coupling molecule; contacting the substrate a carboxylic acid activating compound; contacting the substrate with a photoactive coupling formulation comprising a photoactive compound, a protected coupling molecule, a polymer, and a solvent; selectively exposing the photoactive coupling formulation to light, thereby deprotecting the protected coupling molecule at a selectively exposed area; coupling the unprotected coupling molecule to at least one of the plurality of carboxylic acid groups at the selectively exposed area; and optionally repeating the method to produce a desired polymer at the at least one carboxylic acid group.

Another embodiment includes a method of attaching a coupling molecule to a substrate, comprising: obtaining a substrate comprising a plurality of carboxylic acid groups for linking to a coupling molecule; contacting the substrate with a photoactive carboxylic acid activating compound; selectively exposing the photoactive carboxylic acid activating compound to light, thereby generating carbodiimide at a selectively exposed area and activating the carboxylic acid groups on the substrate; contacting the substrate with a coupling formulation comprising an unprotected coupling molecule, a polymer, and a solvent; coupling the unprotected coupling molecule to at least one of the plurality of carboxylic acid groups at the selectively exposed area; and optionally repeating the method to produce a desired polymer at the at least one carboxylic acid group.

In an embodiment, the coupling step has an efficiency of at least 98%. In an embodiment, the coupling molecule is an amino acid. In an embodiment, the polymer is a polypeptide. In an embodiment, the substrate comprises a porous layer comprising a plurality of attachment sites extending in multiple dimensions from the surface of the porous layer within and around the porous layer. In an embodiment, the attachment site comprises an unprotected carboxylic acid group for binding to the coupling molecule.

In some embodiments, the substrate comprises a planar layer comprising a metal or silicon and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between 1,000-5,000 angstroms, wherein the surface of each pillar is parallel to the upper surface of the layer, and wherein the plurality of pillars are present at a density of greater than 10,000/cm$^2$, and wherein the attachment site is coupled to the upper surface of the pillar.

Another embodiment includes a method of producing a three-dimensional array of features, comprising: obtaining a porous layer comprising a plurality of unprotected carboxylic acid groups; and attaching the features to the unprotected carboxylic acid groups, the features each comprising a collection of peptide chains of determinable sequence and intended length. In some embodiments, the carboxylic acid groups are oriented in multiple directions.

In some embodiments, within an individual feature, the fraction of peptide chains within the collection having the intended length is characterized by an average coupling efficiency for each coupling step of at least 98%. In some embodiments, the features are attached to the surface using a coupling formulation comprising a solvent, a polymer, a coupling molecule, a neutralization reagent, and a coupling reagent.

One further embodiment includes a method of detecting biomolecules in a sample, comprising: providing a substrate comprising at least one porous layer, wherein the layer comprises a plurality of peptide chains attached to carboxylic acid groups, wherein the peptide chains have a known sequence according to positionally-defined locations; contacting the substrate with the sample; and detecting binding events of biomolecules within the sample to the peptide chains. In some embodiments, the carboxylic acid groups are oriented in multiple directions.

In an embodiment, the sample is a biological sample. In an embodiment, the biological sample is a bodily fluid. In some embodiments, the bodily fluid is amniotic fluid, aqueous humour, vitreous humour, bile, blood serum, breast milk, cerebrospinal fluid, cerumen, chyle, endolymph, perilymph, feces, female ejaculate, gastric acid, gastric juice, lymph, mucus, peritoneal fluid, pleural fluid, pus, saliva, sebum, semen, sweat, synovial fluid, tears, vaginal secretion, vomit, or urine. In some embodiments, the biomolecule is a protein. In some embodiments, the biomolecule is an antibody.

In some embodiments, the method has a greater than 40 fold increase in sensitivity of biomolecule detection as compared to a substrate comprising peptide chains attached to a planar layer.

BRIEF DESCRIPTION OF THE SEVERAL VIEWS OF THE DRAWINGS

These and other features, embodiments, and advantages of the present invention will become better understood with regard to the following description, and accompanying drawings, where:

FIG. 1A-1C shows (A) wafer substrate preparation, (B) pillar substrate, and (C) AFM-measured roughness and calculated density of substrate, according to some embodiments.

FIG. 2 shows peptide array synthesis, according to an embodiment.

Figure 1B:
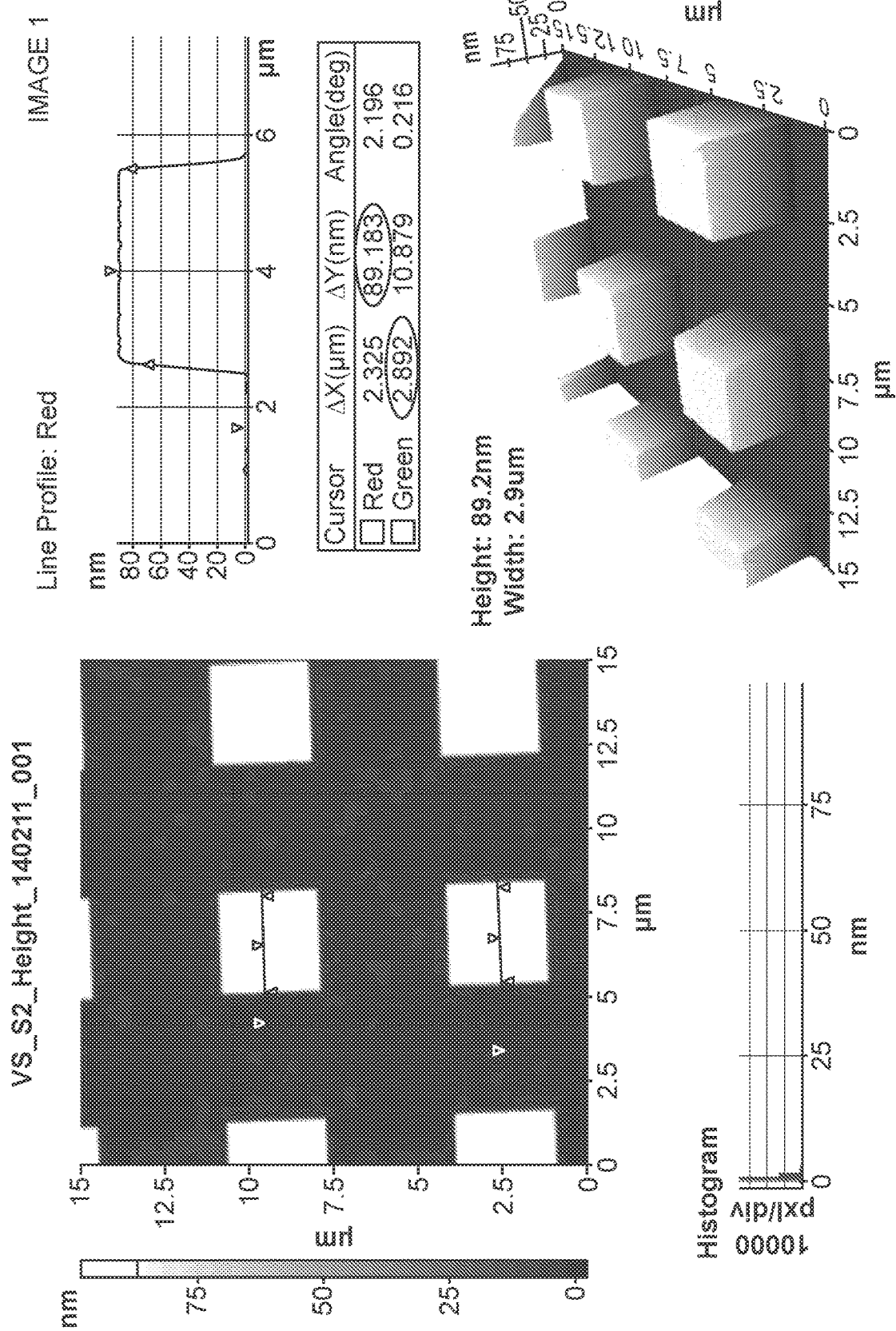

One skilled in the art will readily recognize from the following discussion that alternative embodiments of the structures and methods illustrated herein may be employed without departing from the principles of the invention described herein.

DETAILED DESCRIPTION

Terms used in the claims and specification are defined as set forth below unless otherwise specified.

As used herein the term "wafer" refers to a slice of semiconductor material, such as a silicon or a germanium crystal generally used in the fabrication of integrated circuits. Wafers can be in a variety of sizes from, e.g., 25.4 mm (1 inch) to 300 mm (11.8 inches) along one dimension with thickness from, e.g., 275 μm to 775 μm.

As used herein the term "photoresist" or "resist" or "photoactive material" refers to a light-sensitive material that changes its solubility in a solution when exposed to ultra violet or deep ultra violet radiation. Photoresists are organic or inorganic compounds that are typically divided into two types: positive resists and negative resists. A positive resist is a type of photoresist in which the portion of the photoresist that is exposed to light becomes soluble to the photoresist developer. The portion of the photoresist that is unexposed remains insoluble to the photoresist developer. A negative resist is a type of photoresist in which the portion of the photoresist that is exposed to light becomes insoluble to the photoresist developer. The unexposed portion of the photoresist is dissolved by the photoresist developer.

As used herein the term "photomask" or "reticle" or "mask" refers to an opaque plate with transparent patterns or holes that allow light to pass through. In a typical exposing process, the pattern on a photomask is transferred onto a photoresist As used herein the term "photoactive compound" refers to compounds that are modified when exposed to electromagnetic radiation. These compounds include, for example, cationic photoinitiators such as photoacid or photobase generators, which generate an acid or a base, respectively, when exposed to electromagnetic radiation. A photoinitiator is a compound especially added to a formulation to convert electromagnetic radiation into chemical energy in the form of initiating species, e.g., free radicals or cations. The acid, base, or other product of a photoactive compound exposed to electromagnetic radiation may then react with another compound in a chain reaction to produce a desired chemical reaction. The spatial orientation of the occurrence of these chemical reactions is thus defined according to the pattern of electromagnetic radiation the solution or surface comprising photoactive compounds is exposed to. This pattern may be defined, e.g., by a photomask or reticle.

As used herein the term "coupling molecule" or "monomer molecule" includes any natural or artificially synthesized amino acid with its amino group protected with a fluorenylmethyloxycarbonyl (Fmoc or F-Moc) group or a t-butoxycarbonyl (tboc or Boc) group. These amino acids may have their side chains protected as an option. Examples of coupling molecules include Boc-Gly-OH, Fmoc-Trp-OH. Other examples are described below.

As used here in the term "coupling" or "coupling process" or "coupling step" refers to a process of forming a bond between two or more molecules such as a linking molecule or a coupling molecule. A bond can be a covalent bond such as a peptide bond. A peptide bond is a chemical bond formed between two molecules when the carboxyl group of one coupling molecule reacts with the amino group of the other coupling molecule, releasing a molecule of water ($H_2O$). This is a dehydration synthesis reaction (also known as a condensation reaction), and usually occurs between amino acids. The resulting —C(=O)NH— bond is called a peptide bond, and the resulting molecule is an amide.

As used herein the term "coupling efficiency" refers to the probability of successful addition of a monomer to a reaction site (e.g., at the end of a polymer) available for binding to the monomer. For example, during the growth of a peptide chain in the N to C orientation, a polypeptide having a free carboxyl group would bind to an amino acid having a free amine group under appropriate conditions. The coupling efficiency gives the probability of the addition of a free amino acid to the free carboxyl group under certain conditions. It may be determined in bulk, e.g., by monitoring single monomer additions to several unique reaction sites simultaneously.

As used herein the terms "polypeptide," "peptide," or "protein" are used interchangeably to describe a chain or polymer of amino acids that are linked together by bonds. Accordingly, the term "peptide" as used herein includes a dipeptide, tripeptide, oligopeptide, and polypeptide. The term "peptide" is not limited to any particular number of amino acids. In some embodiments, a peptide contains about 2 to about 50 amino acids, about 5 to about 40 amino acids, or about 5 to about 20 amino acids. A molecule, such as a protein or polypeptide, including an enzyme, can be a "native" or "wild-type" molecule, meaning that it occurs naturally in nature; or it may be a "mutant," "variant," "derivative," or "modification," meaning that it has been made, altered, derived, or is in some way different or changed from a native molecule or from another molecule such as a mutant.

As used herein the term "biomarkers" includes, but is not limited to DNA, RNA, proteins (e.g., enzymes such as kinases), peptides, sugars, salts, fats, lipids, ions and the like.

As used herein the term "linker molecule" or "spacer molecule" includes any molecule that does not add any functionality to the resulting peptide but spaces and extends the peptide out from the substrate, thus increasing the distance between the substrate surface and the growing peptide. This generally reduces steric hindrance with the substrate for reactions involving the peptide (including uni-molecular folding reactions and multi-molecular binding reactions) and so improves performance of assays measuring one or more embodiments of peptide functionality.

As used herein the term "developer" refers to a solution that can selectively dissolve the materials that are either exposed or not exposed to light. Typically developers are water-based solutions with minute quantities of a base added. Examples include tetramethyl ammonium hydroxide in water-based developers. Developers are used for the initial pattern definition where a commercial photoresist is used.

As used herein the term "protecting group" includes a group that is introduced into a molecule by chemical modification of a functional group to obtain chemoselectivity in a subsequent chemical reaction. Chemoselectivity refers to directing a chemical reaction along a desired path to obtain a pre-selected product as compared to another. For example, the use of tboc as a protecting group enables chemoselectivity for peptide synthesis using a light mask and a photoacid generator to selectively remove the protecting group and direct predetermined peptide coupling reactions to occur at locations defined by the light mask.

As used herein the term "microarray," "array" or "chip" refers to a substrate on which a plurality of probe molecules of protein or specific DNA binding sequences have been affixed at separate locations in an ordered manner thus forming a microscopic array. Protein or specific DNA binding sequences may be bound to the substrate of the chip through one or more different types of linker molecules. A "chip array" refers to a plate having a plurality of chips, for example, 24, 96, or 384 chips.

As used herein the term "probe molecules" refers to, but is not limited to, proteins, DNA binding sequences, antibodies, peptides, oligonucleotides, nucleic acids, peptide nucleic acids ("PNA"), deoxyribonucleic acids (DNA), ribonucleic acids (RNA), peptide mimetics, nucleotide mimetics, chelates, biomarkers and the like. As used herein, the term "feature" refers to a particular probe molecule that has been attached to a microarray. As used herein, the term "ligand" refers to a molecule, agent, analyte or compound of interest that can bind to one or more features.

As used herein the term "microarray system" or a "chip array system" refers to a system usually comprised of bio molecular probes formatted on a solid planar surface like glass, plastic or silicon chip plus the instruments needed to handle samples (automated robotics), to read the reporter molecules (scanners) and analyze the data (bioinformatic tools).

As used herein the term "patterned region" or "pattern" or "location" refers to a region on the substrate on which are grown different features. These patterns can be defined using photomasks.

As used herein the term "derivatization" refers to the process of chemically modifying a surface to make it suitable for biomolecular synthesis. Typically derivatization includes the following steps: making the substrate hydrophilic, adding an amino silane group, and attaching a linker molecule.

As used herein the term "capping" or "capping process" or "capping step" refers to the addition of a molecule that prevents the further reaction of the molecule to which it is attached. For example, to prevent the further formation of a peptide bond, the amino groups are typically capped with an acetic anhydride molecule. In other embodiments, ethanolamine is used.

As used herein the term "diffusion" refers to the spread of, e.g., photoacid or photobase through random motion from regions of higher concentration to regions of lower concentration.

As used herein the term "dye molecule" refers to a dye which typically is a colored substance that can bind to a substrate. Dye molecules can be useful in detecting binding between a feature on an array and a molecule of interest.

As used herein, the terms "immunological binding" and "immunological binding properties" refer to the non-covalent interactions of the type which occur between an immunoglobulin molecule and an antigen for which the immunoglobulin is specific.

As used herein the term "biological sample" refers to a sample derived from biological tissue or fluid that can be assayed for an analyte(s) of interest. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect analyte(s) of interest in samples from any organism (e.g., mammal, bacteria, virus, algae, or yeast) or mammal, such as dogs, cats, sheep, cattle, and pigs. The sample may be pretreated as necessary by dilution in an appropriate buffer solution or concentrated, if desired.

As used herein, the term "assay" refers to a type of biochemical test that measures the presence or concentration of a substance of interest in solutions that can contain a complex mixture of substances.

The term "antigen" as used herein refers to a molecule that triggers an immune response by the immune system of a subject, e.g., the production of an antibody by the immune system. Antigens can be exogenous, endogenous or auto antigens. Exogenous antigens are those that have entered the body from outside through inhalation, ingestion or injection. Endogenous antigens are those that have been generated within previously-normal cells as a result of normal cell metabolism, or because of viral or intracellular bacterial infection. Auto antigens are those that are normal protein or protein complex present in the host body but can stimulate an immune response.

As used herein the term "epitope" or "immunoactive regions" refers to distinct molecular surface features of an antigen capable of being bound by component of the adaptive immune system, e.g., an antibody or T cell receptor. Antigenic molecules can present several surface features that can act as points of interaction for specific antibodies. Any such distinct molecular feature can constitute an epitope. Therefore, antigens have the potential to be bound by several distinct antibodies, each of which is specific to a particular epitope.

As used herein the term "antibody" or "immunoglobulin molecule" refers to a molecule naturally secreted by a particular type of cells of the immune system: B cells. There are five different, naturally occurring isotypes of antibodies, namely: IgA, IgM, IgG, IgD, and IgE.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

Unless otherwise noted, "alkyl" as used herein, whether used alone or as part of a substituent group, refers to a saturated, branched, or straight-chain monovalent hydrocarbon radical derived by the removal of one hydrogen atom from a single carbon atom of a parent alkane. Typical alkyl groups include, but are not limited to, methyl; ethyls; propyls such as propan-1-yl, propan-2-yl; butyls such as butan-1-yl, butan-2-yl, 2-methyl-propan-1-yl, 2-methyl-propan-2-yl, and the like. In preferred embodiments, the alkyl groups are $C_{1-6}$alkyl, with $C_{1-3}$alkyl being particularly preferred. "Alkoxyl" radicals are oxygen ethers formed from the previously described straight or branched chain alkyl groups.

The term "aryl," as used herein, refers to aromatic groups comprising a stable six-membered monocyclic, or ten-membered bicyclic or fourteen-membered tricyclic aromatic ring system which consists of carbon atoms. Examples of aryl groups include, but are not limited to, phenyl or naphthalenyl.

The term "cis-trans isomer" refers to stereoisomeric olefins or cycloalkanes (or hetero-analogues) which differ in the positions of atoms (or groups) relative to a reference plane: in the cis-isomer the atoms of highest priority are on the same side; in the trans-isomer they are on opposite sides.

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

The term "oxo" whether used alone or as part of a substituent group refers to an O= bounded to either a carbon or a sulfur atom. For example, phthalimide and saccharin are examples of compounds with oxo substituents.

It must be noted that, as used in the specification and the appended claims, the singular forms "a," "an," and "the" include plural referents unless the context clearly dictates otherwise.

Carbodiimide Precursor Compounds

In some embodiments, the photoactive carboxylic acid activating compound comprises a carbodiimide precursor compound of formula (I):

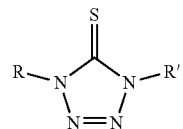

wherein

R is selected from a group comprising substituted or unsubstituted alkyl, and R further comprises a water-solubilizing group; and R' is substituted or unsubstituted aryl.

In certain embodiments, the carboxylic acid activating compound, also referred to as a "coupling reagent" herein, is a carbodiimide. In some embodiments, the polymer is polymethyl methacrylate.

Representative photoactive carboxylic acid activating compound related to the present invention are listed in Table 1.

TABLE 1

Carbodiimide Precursor Compounds

| Compound # | R | R' | Name |
|---|---|---|---|
| 1 | Et₂N-CH₂CH₂CH₂- | 2-methoxyphenyl | 1-(3-(diethylamino)propyl)-4-(2-methoxyphenyl)-1,4-dihydro-5H-tetrazole-5-thione |
| 2 | Et₂N-CH₂- | phenyl | 1-((diethylamino)methyl)-4-phenyl-1,4-dihydro-5H-tetrazole-5-thione |
| 3 | Et₂N-CH₂CH₂CH₂- | phenyl | 1-(3-(diethylamino)propyl)-4-phenyl-1,4-dihydro-5H-tetrazole-5-thione |
| 4 | Et₂N-CH₂CH₂CH₂- | 4-methoxyphenyl | 1-(3-(diethylamino)propyl)-4-(methoxyphenyl)-1,4-dihydro-5H-tetrazole-5-thione |
| 5 | Et₂N-CH₂CH₂CH₂- | 4-(dimethylamino)phenyl | 1-(3-(diethylamino)propyl)-4-(dimethylamino-phenyl)-1,4-dihydro-5H-tetrazole-5-thione |
| 6 | Et₂N-CH₂CH₂CH₂- | 4-(methylthio)phenyl | 1-(3-(diethylamino)propyl)-4-(methylthio-phenyl)-1,4-dihydro-5H-tetrazole-5-thione |
| 7 | Et₂N-CH₂CH₂CH₂- | 4-nitrophenyl | 1-(3-(diethylamino)propyl)-4-(nitrophenyl)-1,4-dihydro-5H-tetrazole-5-thione |

TABLE 1-continued

Carbodiimide Precursor Compounds

| Compound # | R | R' | Name |
|---|---|---|---|
| 8 | diethylamino-propyl | 4-ethoxyphenyl | 1-(3-(diethylamino)propyl)-4-(ethoxyphenyl)-1,4-dihydro-5H-tetrazole-5-thione |
| 9 | diethylamino-propyl | [1,1'-biphenyl]-4-yl | 1-([1,1'-biphenyl]-4-yl)-4-(3-(diethylamino)propyl)-1,4-dihydro-5H-tetrazole-5-thione |

Synthesis of Carbodiimide Precursor Compounds

This application provides methods of making the disclosed compounds according to traditional organic synthetic methods as well as matrix or combinatorial synthetic methods. Scheme 1 describe suggested synthetic routes. Using the scheme, the guidelines below, and the examples, a person of skill in the art may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by techniques such as preparative chromatography. The compounds may be prepared in racemic form or as individual enantiomers or diasteromers by either stereospecific synthesis or by resolution. The compounds may, for example, be resolved into their component enantiomers or diastereomers by techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Scheme 1 and Examples 1 and 2. Compounds analogous to the target compounds of these examples can be made according to similar routes. The disclosed compounds are useful in the manufacture of microarrays as described herein.

General Guidance

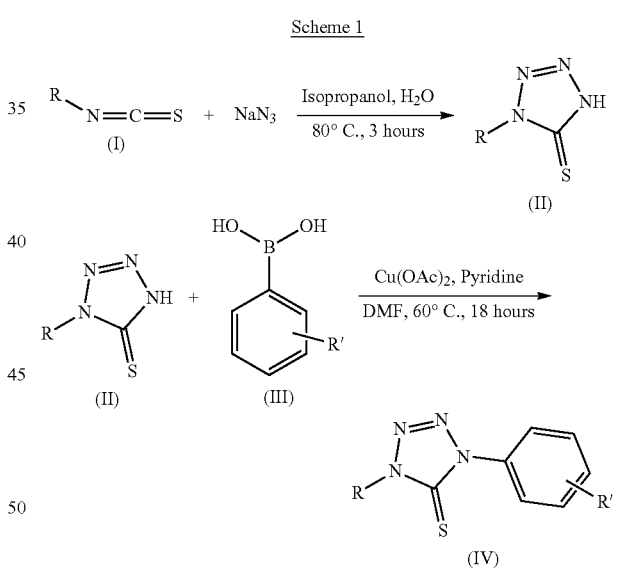

Scheme 1

The compound (I), wherein R is 3-(diethylamino)propyl or 3-(diethylamino)methyl, can be synthesized as outlined by the general synthetic route illustrated in Scheme 1. Treatment of an appropriate isothiocyanate (I) with sodium azide, an known compound prepared by known methods in water solution of isopropanol at 80° Celsius for 3 hours yields the R-substituted 1-hydro-5H-tetrazole-5-thione (II) following a 1,3 dipolar cycloaddition. Copper mediated cross-coupling of the R-substituted 1-hydro-5H-tetrazole-5-thione (II) with phenylboronic acid (III) in the presence of copper acetate, pyridine and dimethylformamide (DMF) at a temperature of 60° Celsius for 18 hours yields compound (IV).

Scheme 1 provides a 70% yield of compound (II) and 33% yield of compound (IV) when R is diethylaminopropyl. The amine of compound (IV) is protonated in the presence of hydrochloride in methanol according to:

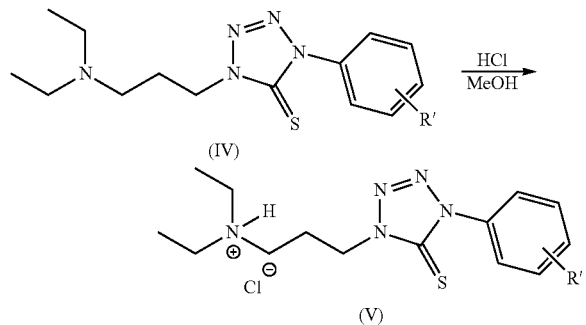

Formation of Carbodiimide

Scheme 2 provides the general scheme of photoactivated carbodiimide formation, e.g. photoinduced formation of hydroxymethyl-phenyl-carbodiimide. Upon radiation exposure at 248 nm the tetrazole thione compounds of formula (I) undergo a ring opening mechanism and release a carbodiimide compound that can be used to activate the carboxylic acid groups of amino acids on the substrate. Upon addition of Hydroxybenzotriazole (HOBt) or 1-hydroxy-7-azabenzotriazole (HOAt) the corresponding esters are formed. The tetrazole thione compounds displays an optimal photolysis performance at 248 nm and can be used to photoactivate an amino acid to form a stable ester that can efficiently be used for coupling. In some embodiments, compound (V) is used according to Scheme 2.

Scheme 2

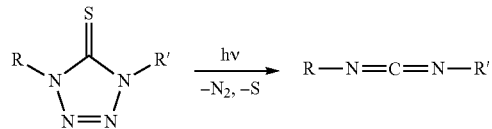

Formulations

Disclosed herein are formulations such as photoactive coupling formulations and linker formulations. These formulations can be useful in the manufacture and/or use of, e.g., substrates and/or peptide arrays disclosed herein. Generally the components of each formulation disclosed herein are soluble in water at room temperature (app. 25° Celsius).

Photoactive Coupling Formulations

Disclosed herein are photoactive coupling formulations. In some embodiments, a photoactive coupling formulation can include components such as a solvent, a coupling reagent or a precursor of a coupling reagent, a coupling molecule, a photoactive compound, and a polymer. In some embodiments, the coupling reagent is identical to the photoactive compound. In some embodiments, the photoactive compound is a carboxylic acid group activating compound.

In some embodiments, a polymer is a non-crosslinking inert polymer. In some embodiments, a polymer is a polyvinyl pyrrolidone. The general structure of polyvinyl pyrrolidone is as follows, where n is any positive integer greater than 1:

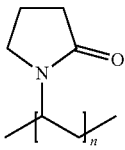

In some embodiments, a polymer is a polymer of vinyl pyrrolidone. In some embodiments, a polymer is polyvinyl pyrrolidone. Poly vinyl pyrrolidone is soluble in water and other polar solvents. When dry it is a light flaky powder, which generally readily absorbs up to 40% of its weight in atmospheric water. In solution, it has excellent wetting properties and readily forms films. In some embodiments, a polymer is a vinyl pyrrolidone or a vinyl alcohol. In some embodiments, a polymer is a polymethyl methacrylate.

In some embodiments, a polymer is 2.5-5% by weight of the total formulation concentration. In some embodiments, a polymer is about 0.5-5% by weight of the total formulation concentration. In some embodiments, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a solvent is water, ethyl lactate, n methyl pyrrollidone or a combination thereof. In some embodiments, ethyl lactate can be dissolved in water to more than 50% to form a solvent. In some embodiments, a solvent can be about 10% propylene glycol methyl ether acetate (PGMEA) and about 90% DI water. In some embodiments, a solvent can include up to about 20% PGMEA. In some embodiments, a solvent can include 50% ethyl lactate and 50% n methyl pyrrollidone. In some embodiments, a solvent is n methyl pyrrollidone. In some embodiments, a solvent is water, an organic solvent, or combination thereof. In some embodiments, the organic solvent is N Methyl pyrrolidone, di methyl formamide or combinations thereof.

In some embodiments, the solvent is about 80-90% by weight of the total formulation concentration. In some embodiments, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

The photoactive coupling formulation comprises coupling molecules. The coupling molecules can include amino acids. In some instances all peptides on an array described herein are composed of naturally occurring amino acids. In others, peptides on an array described herein can be composed of a combination of naturally occurring amino acids and non-naturally occurring amino acids. In other cases, peptides on an array can be composed solely from non-naturally occurring amino acids. Non-naturally occurring amino acids include peptidomimetics as well as D-amino acids. The R group can be found on a natural amino acid or a group that is similar in size to a natural amino acid R group. Additionally, unnatural amino acids, such as beta-alanine, phenylglycine, homoarginine, aminobutyric acid, aminohexanoic acid, aminoisobutyric acid, butylglycine, citrulline, cyclohexylalanine, diaminopropionic acid, hydroxyproline, norleucine, norvaline, ornithine, penicillamine, pyroglutamic acid, sarcosine, and thienylalanine can also be incorporated. These and other natural and unnatural amino acids are available from, for example, EMD Biosciences, Inc., San Diego, Calif. In some embodiments, a coupling molecule comprises a naturally occurring or artificial amino acid or polypeptide. Examples of coupling molecules include Boc-Glycine-OH and Boc-Histidine-OH. In some embodiments, the artificial amino acid is a D-amino acid. In some embodiments, a coupling molecule is 1-2% by weight of the total formulation concentration. In some embodiments, a coupling molecule is about 0.5-5% by weight of the total formulation concentration. In some embodiments, a coupling molecule is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration. In some embodiments, a coupling molecule comprises a protected group, e.g., a group protected via t-Boc or F-Moc (or fmoc) chemistry. In most instances, increasing the concentration of a coupling molecule provides the best performance.

In some embodiments, a coupling reagent is carbodiimide or triazole. In some embodiments, a coupling reagent is 2-4% by weight of the total formulation concentration. In some embodiments, a coupling reagent is about 0.5-5% by weight of the total formulation concentration. In some embodiments, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In any of the combinations above, the formulation can be completely water strippable. Thus, in some embodiments, water can be used to wash away the photoactive coupling formulation after exposure.

Carboxylic Acid Activating Formulations

Disclosed herein are activating formulations for activating carboxylic acid so that it reacts with a free amino group of a biomolecule, e.g., an amino acid, peptide, or polypeptide. An activating formulation can include components such as a carboxylic acid group activating compound and a solvent. In some embodiments, the carboxylic acid group activating compound is a carbodiimide or a carbodiimide precursor. In some embodiments, the carbodiimide is 1-(2-methoxyphenyl)-3-(3-diethylaminopropyl) carbodiimide. In some embodiments, the carboxylic acid group activating compound is selected from: 1-Ethyl-3-(3-dimethylaminopropyl)carbodiimide [EDC], N-hydroxysuccinimide [NHS], 1,3-Diisopropylcarbodiimide [DIC], hydroxybenzotriazole (HOBt), (O-(7-azabenzotriazol-1-yl)-N,N,N',N'-tetramethyluronium hexafluorophosphate) [HATU], benzotriazol-1-yl-oxytripyrrolidinophosphonium hexafluorophosphate [PyBOP], and N,N-Diisopropylethylamine [DIEA]. In some embodiments, the solvent is water. In some embodiments, the solvent is N-methylpyrrolidone (NMP). In some embodiments, the carboxylic acid group activating compound converts the carboxylic acid to a carbonyl group (i.e., carboxylic acid group activation). In some embodiments, the carboxylic acid group is activated for 5, 10, 15, 20, 30, 45, or 60 minutes after exposure to an activation formulation.

In some embodiments, the activating formulation comprises 4% by weight of 1-ethyl-3-(3-dimethylaminopropyl) carbodiimide and 2% by weight of N-hydroxysuccinimide (NHS) dissolved in deionized water. In some embodiments, the activating formulation comprises 4% by weight of 1,3-Diisopropylcarbodiimide (DIC) and 2% by weight of hydroxybenzotriazole (HOBt) dissolved in NMP. In some embodiments, the activating formulation comprises 4% by weight of (O-(7-azabenzotriazol-1-yl)-N,N,N',N'-tetramethyluronium hexafluorophosphate) (HATU) and 2% by weight of N,N-Diisopropylethylamine (DIEA) dissolved in NMP. In some embodiments, the activating formulation comprises 4% by weight of Benzotriazol-1-yl-oxytripyrrolidinophosphonium hexafluorophosphate (PyBOP) and 2% by weight of DIEA dissolved in NMP.

In some embodiments, the carboxylic acid group activating compound is a carbodiimide precursor. In one aspect, the carbodiimide precursor is converted to a carbodiimide through exposure to radiation, e.g., ultraviolet radiation. In one embodiment, the carbodiimide precursor is a thione. The carbodiimide precursor can also be referred to as a photoactivated carbodiimide. In one embodiment, photoactivated carbodiimides are used to provide site-specific activation of carboxylic acid groups on an array by spatially controlling exposure of the photoactivated carbodiimide solution to electromagnetic radiation at a preferred activation wavelength. In some embodiments, the preferred activation wavelength is 248 nm.

In one embodiment, the carbodiimide precursor is a thione that is converted to carbodiimide via photoactivation. In one aspect, the thione is converted to a hydroxymethyl phenyl carbodiimide after exposure to electromagnetic radiation. In some embodiments, the thione is 1-(3-(dimethylamino)propyl)-4-ethyl-1,4-dihydro-5H-tetrazole-5-thione, and others as shown in Table 1.

In some embodiments, the activating solution comprises a carbodiimide precursor, a solvent, and a polymer. In one embodiment, the carbodiimide precursor is 1-(3-(dimethylamino)propyl)-4-ethyl-1,4-dihydro-5H-tetrazole-5-thione. In some embodiments, the carbodiimide precursor is present in the activation solution at a concentration of 2.5% by weight. In some embodiments the carbodiimide precursor is present in the activation solution at a concentration of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or 5.0% by weight of the total formulation concentration.

In some embodiments, the solvent is water. In some embodiments, the solvent is about 80-90% by weight of the total formulation concentration. In some embodiments, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some embodiments, a polymer is a polyvinyl pyrrolidone and/or a polyvinyl alcohol. In some embodiments, a polymer is about 0.5-5% by weight of the total formulation concentration. In some embodiments, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a coupling reagent is a carbodiimide. In some embodiments, a coupling reagent is a triazole. In some embodiments, a coupling reagent is 1-ethyl-3-(3-dimethylaminopropyl) carbodiimide. In some embodiments, a coupling reagent is about 0.5-5% by weight of the total formulation concentration. In some embodiments, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

Linker Formulations

Also disclosed herein is a linker formulation. A linker formulation can include components such as a solvent, a polymer, a linker molecule, and a coupling reagent. In some embodiments, the polymer is 1% by weight polyvinyl alcohol and 2.5% by weight poly vinyl pyrrollidone, the linker molecule is 1.25% by weight polyethylene oxide, the coupling reagent is 1% by weight 1-ethyl-3-(3-dimethylaminopropyl) carbodiimide, and the solvent includes water. In some embodiments, the polymer is 0.5-5% by weight polyvinyl alcohol and 0.5-5% by weight poly vinyl pyrrollidone, the linker molecule is 0.5-5% by weight polyethylene oxide, the coupling reagent is 0.5-5% by weight 1-ethyl-3-(3-dimethylaminopropyl) carbodiimide, and the solvent includes water.

In some embodiments, the solvent is water, an organic solvent, or a combination thereof. In some embodiments, the organic solvent is N methyl pyrrolidone, dimethyl formamide, dichloromethane, dimethyl sulfoxide, or a combination thereof. In some embodiments, the solvent is about 80-90% by weight of the total formulation concentration. In some embodiments, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some embodiments, a polymer is a polyvinyl pyrrolidone and/or a polyvinyl alcohol. The general structure of polyvinyl alcohol is as follows, where n is any positive integer greater than 1:

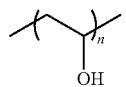

In some embodiments, a polymer is about 0.5-5% by weight of the total formulation concentration. In some embodiments, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

A linker molecule can be a molecule inserted between a surface disclosed herein and peptide that is being synthesized via a coupling molecule. A linker molecule does not necessarily convey functionality to the resulting peptide, such as molecular recognition functionality, but can instead elongate the distance between the surface and the peptide to enhance the exposure of the peptide's functionality region(s) on the surface. In some embodiments, a linker can be about 4 to about 40 atoms long to provide exposure. The linker molecules can be, for example, aryl acetylene, ethylene glycol oligomers containing 2-10 monomer units (PEGs), diamines, diacids, amino acids, and combinations thereof. Examples of diamines include ethylene diamine (EDA) and diamino propane. Alternatively, linkers can be the same molecule type as that being synthesized (e.g., nascent polymers or various coupling molecules), such as polypeptides and polymers of amino acid derivatives such as for example, amino hexanoic acids. In some embodiments, a linker molecule is a molecule having a carboxylic group at a first end of the molecule and a protecting group at a second end of the molecule. In some embodiments, the protecting group is a t-Boc protecting group or an Fmoc protecting group. In some embodiments, a linker molecule is or includes an aryl acetylene, a polyethyleneglycol, a nascent polypeptide, a diamine, a diacid, a peptide, or combinations thereof. In some embodiments, a linker molecule is about 0.5-5% by weight of the total formulation concentration. In some embodiments, a linker molecule is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

The unbound (or free end) portion of a linker molecule can have a reactive functional group which is blocked, protected, or otherwise made unavailable for reaction by a removable protecting group. The protecting group can be bound to a linker molecule to protect a reactive functionality on the linker molecule. Protecting groups that can be used include all acid- and base-labile protecting groups. For example, linker amine groups can be protected by t-butoxycarbonyl (t-BOC or BOC) or benzyloxycarbonyl (CBZ), both of which are acid labile, or by 9-fluorenylmethoxycarbonyl (FMOC), which is base labile.

Additional protecting groups that can be used include acid-labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, alpha,alpha-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9 fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid-labile groups for protecting carboxylic acids: tert-butyl ester; acid labile groups for protecting hydroxyl groups: dimethyltrityl. See also, Greene, T. W., Protective Groups in Organic Synthesis, Wiley-Interscience, N.Y., (1981).

Substrates

Also disclosed herein are substrates. In some embodiments a substrate surface is planar (i.e., 2-dimensional). In some embodiments a substrate surface is functionalized with free carboxylic acid groups. In some embodiments, a substrate surface is functionalized with free amine groups. A surface that is functionalized with free amine groups can be converted to free carboxylic acid groups by reacting with activating the carboxylic acid groups of a molecule comprising at least two free carboxylic acid groups (e.g., converting the carboxylic acid group to a carbonyl group using carbodiimide) and reacting the molecule with the free amine groups attached to the surface of the substrate. In some embodiments, the molecule comprising multiple carboxylic acid groups is succinic anhydride, polyethylene glycol diacid, benzene-1,3,5-tricarboxylic acid, benzenehexacarboxylic acid, or carboxymethyl dextran.

In some embodiments, a substrate can include a porous layer (i.e., a 3-dimensional layer) comprising functional groups for binding a first monomer building block. In some embodiments, a substrate surface comprises pillars for peptide attachment or synthesis. In some embodiments, a porous layer is added to the top of the pillars.

Porous Layer Substrates

Porous layers that can be used are flat, permeable, polymeric materials of porous structure that have a carboxylic acid functional group (that is native to the constituent polymer or that is introduced to the porous layer) for attachment of the first peptide building block. For example, a porous layer can be comprised of porous silicon with functional groups for attachment of a polymer building block attached to the surface of the porous silicon. In another example, a porous layer can comprise a cross-linked polymeric material. In some embodiments, the porous layer can employ polystyrenes, saccharose, dextrans, polyacryloyl-morpholine, polyacrylates, polymethylacrylates, polyacrylamides, polyacrylolpyrrolidone, polyvinylacetates, polyethyleneglycol, agaroses, sepharose, other conventional chromatography type materials and derivatives and mixtures thereof. In some embodiments, the porous layer building material is selected from: poly(vinyl alcohol), dextran, sodium alginate, poly(aspartic acid), poly(ethylene glycol), poly(ethylene oxide), poly(vinyl pyrrolidone), poly(acrylic acid), poly(acrylic acid)-sodium salt, poly(acrylamide), poly(N-isopropyl acrylamide), poly(hydroxyethyl acrylate), poly (acrylic acid), poly(sodium styrene sulfonate), poly(2-acrylamido-2-methyl-1-propanesulfonic acid), polysaccharides, and cellulose derivatives. Preferably the porous layer has a porosity of 10-80%. In one embodiment, the thickness of the porous layer ranges from 0.01 µm to about 1,000 µm. Pore sizes included in the porous layer may range from 2 nm to about 100 µm.

According to another embodiment of the present invention there is provided a substrate comprising a porous polymeric material having a porosity from 10-80%, wherein reactive groups are chemically bound to the pore surfaces and are adapted in use to interact, e.g. by binding chemically, with a reactive species, e.g., deprotected monomeric building blocks or polymeric chains. In one embodiment the reactive group is a carboxylic acid group. The carboxylic acid group is free to bind, for example, an unprotected amine group of a peptide or polypeptide.

In an embodiment, the porous layer is in contact with a support layer. The support layer comprises, for example, metal, plastic, silicon, silicon oxide, or silicon nitride. In another embodiment, the porous layer can be in contact with a patterned surface, such as on top of pillar substrates described below.

Pillar Substrates

In some embodiments, a substrate can include a planar layer comprising a metal or silicon and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between about 1,000-5,000 angstroms, and wherein the plurality of pillars are present at a density of greater than about 10,000/$cm^2$.

In some embodiments, the distance between the surface of each pillar and the upper surface of the later can be between about less than 1,000, 2,000, 3,000, 3,500, 4,500, 5,000, or greater than 5,000 angstroms (or any integer in between).

In some embodiments, the surface of each pillar is parallel to the upper surface of the layer. In some embodiments, the surface of each pillar is substantially parallel to the upper surface of the layer.

In some embodiments, the plurality of pillars are present at a density of greater than 500, 1,000, 2,000, 3,000, 4,000, 5,000, 6,000, 7,000, 8,000, 9,000, 10,000, 11,000, or 12,000/$cm^2$ (or any integer in between). In some embodiments, the plurality of pillars are present at a density of greater than 10,000/$cm^2$. In some embodiments, the plurality of pillars are present at a density of about 10,000/$cm^2$ to about 2.5 million/$cm^2$ (or any integer in between). In some embodiments, the plurality of pillars are present at a density of greater than 2.5 million/$cm^2$.

In some embodiments, the surface area of each pillar surface is at least 1 $\mu m^2$. In some embodiments, the surface area of each pillar surface can be at least 0.1, 0.5, 12, 3, 4, 5, 6, 7, 8, 9, 10, 15, 20, 25, 30, 35, 40, 45, or 50 $\mu m^2$ (or any integer in between). In some embodiments, the surface area of each pillar surface has a total area of less than 10,000 $\mu m^2$. In some embodiments, the surface area of each pillar surface has a total area of less than 500, 1,000, 2,000, 3,000, 4,000, 5,000, 6,000, 7,000, 8,000, 9,000, 10,000, 11,000, or 12,000 $\mu m^2$ (or any integer in between).

In some embodiments, the distance between the surface of each pillar and the lower surface of the layer is 2,000-7,000 angstroms. In some embodiments, the distance between the surface of each pillar and the lower surface of the layer is about less than 500, 1,000, 2,000, 3,000, 4,000, 5,000, 6,000, 7,000, 8,000, 9,000, 10,000, 11,000, 12,000, or greater than 12,000 angstroms (or any integer in between). In some embodiments, the distance between the surface of each pillar and the lower surface of the layer is 7,000, 3,000, 4,000, 5,000, 6,000, or 7,000 angstroms (or any integer in between).

In some embodiments, the layer is 1,000-2,000 angstroms thick. In some embodiments, the layer is about less than 500, 1,000, 2,000, 3,000, 4,000, 5,000, 6,000, 7,000, 8,000, 9,000, 10,000, 11,000, 12,000, or greater than 12,000 angstroms thick (or any integer in between).

In some embodiments, the center of each pillar is at least 2,000 angstroms from the center of any other pillar. In some embodiments, the center of each pillar is at least about 500, 1,000, 2,000, 3,000, or 4,000 angstroms (or any integer in between) from the center of any other pillar. In some embodiments, the center of each pillar is at least about 2 µm to 200 µm from the center of any other pillar.

In some embodiments, at least one or each pillar comprises silicon. In some embodiments, at least one or each pillar comprises silicon dioxide or silicon nitride. In some embodiments, at least one or each pillar is at least 90, 91, 92, 93, 94, 95, 96, 97, 98, 98.5, or 99% (by weight) silicon dioxide.

In some embodiments, a substrate can include a linker molecule having a free amino terminus attached to the surface of each pillar. In some embodiments, a substrate can include a linker molecule having a free amino terminus attached to the surface of at least one pillar. In some embodiments, a substrate can include a linker molecule having a protecting group attached to the surface of each pillar. In some embodiments, a substrate can include a linker molecule having a protecting group attached to the surface of at least one pillar. In some embodiments, a substrate can include a coupling molecule attached to the surface of at least one pillar. In some embodiments, a substrate can include a coupling molecule attached to the surface of each pillar. In some embodiments, a substrate can include a polymer in contact with the surface of at least one of the pillars. In some embodiments, a substrate can include a polymer in contact with the surface of each pillar. In some embodiments, a substrate can include a gelatinous form of a polymer in contact with the surface of at least one of the pillars. In some embodiments, a substrate can include a solid form of a polymer in contact with the surface of at least one of the pillars.

In some embodiments, the surface of at least one of the pillars of the substrate is derivatized. In some embodiments, a substrate can include a polymer chain attached to the surface of at least one of the pillars. In some embodiments, the polymer chain comprises a peptide chain. In some embodiments, the attachment to the surface of the at least one pillar is via a covalent bond.

In some embodiments, the surface of each pillar is square or rectangular in shape. In some embodiments, the substrate can be coupled to a silicon dioxide layer. The silicon dioxide layer can be about 0.5 µm to 3 µm thick. In some embodiments, the substrate can be coupled to a wafer, e.g., a silicon wafer. The silicon dioxide layer can be about 700 µm to 750 µm thick.

Arrays

Also disclosed herein are arrays. In some embodiments, the surface of the array is functionalized with free carboxylic acids. In some embodiments, the free carboxylic acids are activated to bind to amine groups, e.g., during polypeptide synthesis on the surface of the array. In some embodiments, the surface density of free carboxylic acid groups on the array is greater than $10/cm^2$, $100/cm^2$, $1,000/cm^2$, $10,000/cm^2$, $100,000/cm^2$, $1,000,000/cm^2$, or $10,000,000/cm^2$.

In some embodiments, an array can be a three-dimensional array, e.g., a porous array comprising features attached to the surface of the porous array. In some embodiments, the surface of a porous array includes external surfaces and surfaces defining pore volume within the porous array. In some embodiments, a three-dimensional array can include features attached to a surface at positionally-defined locations, said features each comprising: a collection of peptide chains of determinable sequence and intended length. In one embodiment, within an individual feature, the fraction of peptide chains within said collection having the intended length is characterized by an average coupling efficiency for each coupling step of greater than 98%.

In some embodiments, the average coupling efficiency for each coupling step is at least 98.5%. In some embodiments, the average coupling efficiency for each coupling step is at least 99%. In some embodiments, the average coupling efficiency for each coupling step is at least 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%.

In some embodiments, each peptide chain is from 5 to 60 amino acids in length. In some embodiments, each peptide chain is at least 5 amino acids in length. In some embodiments, each peptide chain is at least 5, 10, 15, 20, 25, 30, 35, 40, 45, 50, 55, or 60 amino acids in length. In some embodiments, each peptide chain is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, each peptide chain comprises one or more L amino acids. In some embodiments, each peptide chain comprises one or more D amino acids. In some embodiments, each peptide chain comprises one or more naturally occurring amino acids. In some embodiments, each peptide chain comprises one or more synthetic amino acids.

In some embodiments, an array can include at least 1,000 different peptide chains attached to the surface. In some embodiments, an array can include at least 10,000 different peptide chains attached to the surface. In some embodiments, an array can include at least 100, 500, 1000, 2000, 3000, 4000, 5000, 6000, 7000, 8000, 9000, 10,000, or greater than 10,000 different peptide chains attached to the surface (or any integer in between).

In some embodiments, each of the positionally-defined locations is at a different, known location that is physically separated from each of the other positionally-defined locations. In some embodiments, each of the positionally-defined locations is a positionally-distinguishable location. In some embodiments, each determinable sequence is a known sequence. In some embodiments, each determinable sequence is a distinct sequence.

In some embodiments, the features are covalently attached to the surface. In some embodiments, said peptide chains are attached to the surface through a linker molecule or a coupling molecule.

In some embodiments, the features comprise a plurality of distinct, nested, overlapping peptide chains comprising subsequences derived from a source protein having a known sequence. In some embodiments, each peptide chain in the plurality is substantially the same length. In some embodiments, each peptide chain in the plurality is the same length. In some embodiments, each peptide chain in the plurality is at least 5 amino acids in length. In some embodiments, each peptide chain in the plurality is at least 5, 10, 15, 20, 25, 30, 35, 40, 45, 50, 55, or 60 amino acids in length. In some embodiments, each peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, at least one peptide chain in the plurality is at least 5 amino acids in length. In some embodiments, at least one peptide chain in the plurality is at least 5, 10, 15, 20, 25, 30, 35, 40, 45, 50, 55, or 60 amino acids in length. In some embodiments, at least one peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, each polypeptide in a feature is substantially the same length. In some embodiments, each polypeptide in a feature is the same length. In some embodiments, the features comprise a plurality of peptide chains each having a random, determinable sequence of amino acids.

Methods

Methods of Manufacturing Substrates

Also disclosed herein are methods for making substrates. In some embodiments, a method of producing a substrate can include coupling a porous layer to a support layer. The support layer can comprise any metal or plastic or silicon or silicon oxide or silicon nitride. In one embodiment, the substrate comprises multiple carboxylic acid substrates attached to the substrate for binding peptides during peptide synthesis and protein coupling. In some embodiments, a method of producing a substrate can include coupling a porous layer to a plurality of pillars, wherein the porous layer comprises functional groups for attachment of a compound to the substrate, wherein the plurality of pillars are coupled to a planar layer in positionally-defined locations, wherein each pillar has a planar surface extended from the planar layer, wherein the distance between the surface of each pillar and the upper surface of the planar layer is between about 1,000-5,000 angstroms, and wherein the plurality of pillars are present at a density of greater than about 10,000/cm$^2$.

In some embodiments, the surface of each pillar is parallel to the upper surface of the planar layer. In some embodiments, the surface of each pillar is substantially parallel to the upper surface of the planar layer.

In some embodiments, a method of preparing a substrate surface can include obtaining a surface comprising silicon dioxide and contacting the surface with a photoactive coupling formulation comprising a photoactive compound, a coupling molecule, a coupling reagent, a polymer, and a solvent; and applying ultraviolet light to positionally-defined locations located on the top of the surface and in contact with the photoactive formulation.

Methods of Manufacturing Arrays

Also disclosed herein are methods for manufacturing arrays. In some embodiments, the arrays disclosed herein can be synthesized in situ on a surface, e.g., a substrate disclosed herein. In some instances, the arrays are made using photolithography. For example, the substrate is contacted with a photoactive coupling solution. Masks can be used to control radiation or light exposure to specific locations on a surface provided with free linker molecules or free coupling molecules having protecting groups. In the exposed locations, the protecting groups are removed, resulting in one or more newly exposed reactive moieties on the coupling molecule or linker molecule. The desired linker or coupling molecule is then coupled to the unprotected attached molecules, e.g., at the carboxylic acid group. The process can be repeated to synthesize a large number of features in specific or positionally-defined locations on a surface (see, for example, U.S. Pat. No. 5,143,854 to Pirrung et al., U.S. Patent Application Publication Nos. 2007/0154946 (filed on Dec. 29, 2005), 2007/0122841 (filed on Nov. 30, 2005), 2007/0122842 (filed on Mar. 30, 2006), 2008/0108149 (filed on Oct. 23, 2006), and 2010/0093554 (filed on Jun. 2, 2008), each of which is herein incorporated by reference).

In some embodiments, a method of producing a three-dimensional (e.g., porous) array of features, can include obtaining a porous layer attached to a surface; and attaching the features to the porous layer, said features each comprising a collection of peptide chains of determinable sequence and intended length, wherein within an individual feature, the fraction of peptide chains within said collection having the intended length is characterized by an average coupling efficiency for each coupling step of at least about 98%. In some embodiments, the features are attached to the surface using a photoactive coupling formulation, comprising a photoactive compound, a coupling molecule, a coupling reagent, a polymer, and a solvent. In some embodiments, the features are attached to the surface using a photoactive coupling formulation disclosed herein. In some embodiments, the photoactive coupling formulation is stripped away using water.

In one embodiment, described herein is a process of manufacturing an array. A surface comprising attached carboxylic acid groups is provided. The surface is contacted with a photoactive coupling solution comprising a photoactive compound, a coupling molecule, a coupling reagent, a polymer, and a solvent. The surface is exposed to ultraviolet light in a deep ultra violet scanner tool according to a pattern defined by a photomask, wherein the locations exposed to ultraviolet light undergo photo base generation due to the presence of a photobase generator in the photoactive coupling solution. The expose energy can be from 1 mJ/cm$^2$ to 100 mJ/cm$^2$ in order to produce enough photobase.

The surface is post baked upon exposure in a post exposure bake module. Post exposure bake acts as a chemical amplification step. The baking step amplifies the initially generated photobase and also enhances the rate of diffusion to the substrate. The post bake temperature can vary between 75° C. to 115° C., depending on the thickness of the porous surface, for at least 60 seconds and not usually exceeding 120 seconds. The free carboxylic acid group is coupled to the deprotected amine group of a free peptide or polypeptide, resulting in coupling of the free peptide or polypeptide to the carboxylic acid group attached to the surface. This surface may be a porous surface. The synthesis of peptides coupled to a carboxylic acid group attached to the surface occurs in an N→C synthesis orientation, with the amine group of free peptides attaching to carboxylic acid groups bound to the surface of the substrate. Alternatively, a diamine linker may be attached to a free carboxylic acid group to orient synthesis in a C→N direction, with the carboxylic acid group of free peptides attaching to amine groups bound to the surface of the substrate.

The photoactive coupling solution can now be stripped away. In some embodiments, provided herein is a method of stripping the photoresist completely with deionized (DI) water. This process is accomplished in a developer module. The wafer is spun on a vacuum chuck for, e.g., 60 seconds to 90 seconds and deionized water is dispensed through a nozzle for about 30 seconds.

The photoactive coupling formulation can be applied to the surface in a coupling spin module. A coupling spin module can typically have 20 nozzles or more to feed the photoactive coupling formulation. These nozzles can be made to dispense the photoactive coupling formulation by means of pressurizing the cylinders that hold these solutions or by a pump that dispenses the required amount. In some embodiments, the pump is employed to dispense 5-8 cc of the photoactive coupling formulation onto the substrate. The substrate is spun on a vacuum chuck for 15-30 seconds and the photoactive coupling formulation is dispensed. The spin speed can be set to 2000 to 2500 rpm.

Optionally, a cap film solution coat is applied on the surface to prevent the unreacted amino groups on the substrate from reacting with the next coupling molecule. The cap film coat solution can be prepared as follows: a solvent, a polymer, and a coupling molecule. The solvent that can be used can be an organic solvent like N methyl pyrrolidone, dimethyl formamide, or combinations thereof. The capping molecule is typically acetic anhydride and the polymer can be polyvinyl pyrrolidone, polyvinyl alcohol, polymethyl methacrylate, poly (methyl iso propenyl) ketone, or poly (2 methyl pentene 1 sulfone). In some embodiments, the capping molecule is ethanolamine.

This process is done in a capping spin module. A capping spin module can include one nozzle that can be made to dispense the cap film coat solution onto the substrate. This solution can be dispensed through pressurizing the cylinder that stores the cap film coat solution or through a pump that precisely dispenses the required amount. In some embodiments, a pump is used to dispense around 5-8 cc of the cap coat solution onto the substrate. The substrate is spun on a vacuum chuck for 15-30 s and the coupling formulation is dispensed. The spin speed can be set to 2000 to 2500 rpm.

The substrates with the capping solution are baked in a cap bake module. A capping bake module is a hot plate set up specifically to receive wafers just after the capping film coat is applied. In some embodiments, provided herein is a method of baking the spin coated capping coat solution in a hot plate to accelerate the capping reaction significantly. Hot plate baking generally reduces the capping time for amino acids to less than two minutes.

The byproducts of the capping reaction are stripped in a stripper module. A stripper module can include several nozzles, typically up to 10, set up to dispense organic solvents such as acetone, iso propyl alcohol, N methyl pyrrolidone, dimethyl formamide, DI water, etc. In some embodiments, the nozzles can be designated for acetone followed by iso propyl alcohol to be dispensed onto the spinning wafer. The spin speed is set to be 2000 to 2500 rpm for around 20 s.

This entire cycle can be repeated as desired with different coupling molecules each time to obtain a desired sequence.

In some embodiments, an array comprising a surface of free carboxylic acids is used to synthesize polypeptides in an N→C orientation. In one embodiment, the carboxylic acids on the surface of the substrate are activated (e.g., converted to a carbonyl) to allow them to bind to free amine groups on an amino acid. In one embodiment, activation of carboxylic acids on the group of the surface can be done by addition of a solution comprising a carbodiimide or succinimide to the surface of the array. In some embodiments, carboxylic acids can be activated by addition of a solution comprising 1-ethyl-3-(3-dimethylaminopropyl)carbodiimide [EDC], N-hydroxysuccinimide [NHS], 1,3-diisopropylcarbodiimide [DIC], hydroxybenzotriazole (HOBt), (O-(7-azabenzotriazol-1-yl)-N,N,N',N'-tetramethyluronium hexafluorophosphate) [HATU], benzotriazol-1-yl-oxytripyrrolidinophosphonium hexafluorophosphate [PyBOP], or N,N-diisopropylethylamine [DIEA] to the surface of the array. The activation solution is washed away and the surface of the array is prepared for addition of an amino acid layer (i.e., one amino acid at each activated carboxylic acid group). Carboxylic acid groups remain activated for up to 2, 3, 4, 5, 6, 7, 8, 9, or 10 hours.

Addition of a solution comprising an amino acid with a free amine group to the activated carboxylic acid surface of the array results in binding of a single amino acid to each carboxylic acid group. In some embodiments, the amino acid comprises an amino acid with protected amine groups. Using a photosensitive chemical reaction, the protecting group can be removed from the amine group of selected amino acids at site-specific locations using a reticle. For example, Fmoc-protected amino acids are mixed in a solution comprising a photobase generator. Upon exposure of the solution on the array to a specific frequency of light at site-specific locations, the photobase generator will release a base which will deprotect the amino acid, resulting in coupling of the amino acid to the activated carboxylic acid group on the surface of the array. Another method involves using a protected base that is then unprotected by a photoacid released by a photoacid generator upon light exposure. In some embodiments, the protected base is N-Boc-piperidine or 1,4-bis(N-Boc)-piperazine.

After a completed layer of amino acids is coupled, remaining uncoupled activated carboxylic acids are capped to prevent nonspecific binding of amino acids on subsequent synthesis steps. The steps of activation, addition of an amino acid layer, and capping are repeated as necessary to synthesize the desired polypeptides at specific locations on the array.

In one embodiment, peptides synthesized in the N→C terminus direction can be capped with a diamine molecule to enhance binding properties of selected polypeptide sequences to a biological molecule, e.g., an antibody. In other embodiments, peptides synthesized in the C→N direction can be capped with a dicarboxylic acid molecule to enhance binding properties of selected sequences to a biological molecule.

While synthesizing polypeptides in parallel on the surface of an array, the method described herein ensures complete activation of carboxylic acid on the surface of the array. Due to stability of the activated ester for an extended period of time, 2, 3, 4, 5, 6, 7, 8, 9, 10, 11, 12, 13, 14, 15, 16, 17, 18, 19, 20, 21, 22, 23, 24, 25 or more coupling cycles may be completed after a single activation step (e.g., to couple an entire layer of 2-25 or more different amino acids at different locations on the array). As the coupling occurs during hard bake (heating in a hot plate at 85-90° Celsius for 90 seconds immediately after coating) and due to the presence of excess amino acid in the solution, complete 100% deprotection of Fmoc-protected amino acid may not be required for significantly high coupling yields. After addition of all amino acids and capping, all free activated carboxylic acids are either coupled or capped, thus resulting in high efficiency and accuracy of polypeptide synthesis.

Methods of Use of Peptide Arrays

Also disclosed herein are methods of using substrates, formulations, and/or arrays. Uses of the arrays disclosed herein can include research applications, therapeutic purposes, medical diagnostics, and/or stratifying one or more patients.

Any of the arrays described herein can be used as a research tool or in a research application. In one aspect, arrays can be used for high throughput screening assays. For example, enzyme substrates (i.e., peptides on a peptide array described herein) can be tested by subjecting the array to an enzyme and identifying the presence or absence of enzyme substrate(s) on the array, e.g., by detecting at least one change among the features of the array.

Arrays can also be used in screening assays for ligand binding, to determine substrate specificity, or for the identification of peptides that inhibit or activate proteins. Labeling techniques, protease assays, as well as binding assays useful for carrying out these methodologies are generally well-known to one of skill in the art.

In some embodiments, an array can be used to represent a known protein sequence as a sequence of overlapping peptides. For example, the amino acid sequence of a known protein is divided into overlapping sequence segments of any length and of any suitable overlapping frame, and peptides corresponding to the respective sequence segments are in-situ synthesized as disclosed herein. The individual peptide segments so synthesized can be arranged starting from the amino terminus of the known protein.

In some embodiments, an array is used in a method wherein the antigenic representation of the array includes at least one region where the whole antigen sequence of a known protein is spanned via epitope sliding; the immunoactive regions of the antigen are determined by contacting one or more clinical samples on the array or a plurality of different arrays, and the set of peptide sequences required to represent the known protein antigen are reduced.

In some embodiments, a sample is applied to an array having a plurality of random peptides. The random peptides can be screened and BLASTed to determine homologous domains with, e.g., a 90% or more identity to a given antigenic sequence. In some aspect, the whole antigenic sequence can then be synthesized and used to identify potential markers and/or causes of a disease of interest.

In some embodiments, an array is used for high throughput screening of one or more genetic factors. Proteins associated with a gene can be a potential antigen and antibodies against these proteins can be used to estimate the relation between gene and a disease.

In another example, an array can be used to identify one or more biomarkers. Biomarkers can be used for the diagnosis, prognosis, treatment, and management of diseases. Biomarkers may be expressed, or absent, or at a different level in an individual, depending on the disease condition, stage of the disease, and response to disease treatment. Biomarkers can be, e.g., DNA, RNA, proteins (e.g., enzymes such as kinases), sugars, salts, fats, lipids, or ions.

Arrays can also be used for therapeutic purposes, e.g., identifying one or more bioactive agents. A method for identifying a bioactive agent can comprise applying a plurality of test compounds to an array and identifying at least one test compound as a bioactive agent. The test compounds can be small molecules, aptamers, oligonucleotides, chemicals, natural extracts, peptides, proteins, fragment of antibodies, antibody like molecules or antibodies. The bioactive agent can be a therapeutic agent or modifier of therapeutic targets. Therapeutic targets can include phosphatases, proteases, ligases, signal transduction molecules, transcription factors, protein transporters, protein sorters, cell surface receptors, secreted factors, and cytoskeleton proteins.

In another aspect, an array can be used to identify drug candidates for therapeutic use. For example, when one or more epitopes for specific antibodies are determined by an assay (e.g., a binding assay such as an ELISA), the epitopes can be used to develop a drug (e.g., a monoclonal neutralizing antibody) to target antibodies in disease.

In one aspect, also provided are arrays for use in medical diagnostics. An array can be used to determine a response to administration of drugs or vaccines. For example, an individual's response to a vaccine can be determined by detecting the antibody level of the individual by using an array with peptides representing epitopes recognized by the antibodies produced by the induced immune response. Another diagnostic use is to test an individual for the presence of biomarkers, wherein samples are taken from a subject and the sample is tested for the presence of one or more biomarkers.

Arrays can also be used to stratify patient populations based upon the presence or absence of a biomarker that indicates the likelihood a subject will respond to a therapeutic treatment. The arrays can be used to identify known biomarkers to determine the appropriate treatment group. For example, a sample from a subject with a condition can be applied to an array. Binding to the array may indicate the presence of a biomarker for a condition. Previous studies may indicate that the biomarker is associated with a positive outcome following a treatment, whereas absence of the biomarker is associated with a negative or neutral outcome following a treatment. Because the patient has the biomarker, a health care professional may stratify the patient into a group that receives the treatment.

In some embodiments, a method of detecting the presence or absence of a protein of interest (e.g., an antibody) in a sample can include obtaining an array disclosed herein and contacted with a sample suspected of comprising the protein of interest; and determining whether the protein of interest is present in the sample by detecting the presence or absence of binding to one or more features of the array. In some embodiments, the protein of interest can be obtained from a bodily fluid, such as amniotic fluid, aqueous humour, vitreous humour, bile, blood serum, breast milk, cerebrospinal fluid, cerumen, chyle, endolymph, perilymph, feces, female ejaculate, gastric acid, gastric juice, lymph, mucus, peritoneal fluid, pleural fluid, pus, saliva, sebum, semen, sweat, synovial fluid, tears, vaginal secretion, vomit, or urine.

In some embodiments, a method of identifying a vaccine candidate can include obtaining an array disclosed herein contacted with a sample derived from a subject previously administered the vaccine candidate, wherein the sample comprises a plurality of antibodies; and determining the binding specificity of the plurality of antibodies to one or more features of the array. In some embodiments, the features comprise a plurality of distinct, nested, overlapping peptide chains comprising subsequences derived from a source protein having a known sequence.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* 3rd Ed. (Plenum Press) Vols A and B (1992).

Example 1

1-(diethylamino-methyl)-4-phenyl-1,4-dihydro-5H-tetrazole-5-thione

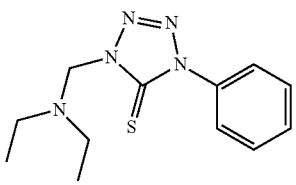 [SMILES: CCN(CC)Cn1nnn(-c2ccccc2)c1=S]

1-(diethylamino-methyl)-4-phenyl-1,4-dihydro-5H-tetrazole-5-thione is commercially available from Sigma Aldrich.

Example 2

1-(3-(diethylamino)-propyl)-4-(2-methoxyphenyl)-1,4-dihydro-5H-tetrazole-5-thione

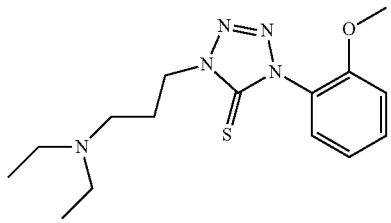 [SMILES: CCN(CC)CCCn1nnn(-c2ccccc2OC)c1=S]

1-(3-(diethylamino)-propyl)-4-(2-methoxyphenyl)-1,4-dihydro-5H-tetrazole-5-thione was prepared according to Scheme 1 with a molecular weight of 321.44 and chemical formula: $C_5H_{23}N_5OS$.

$^1$H NMR (400 MHz, CDCl3): 7.47-7.38 (m, 2H), 7.01-6.95 (m, 2H), 4.43 (t, 2H), 3.83 (s, 3H), 2.62-2.54 (m, 6H), 2.14-2.11 (m, 2H), 1.07-1.04 (t, 6H). MS, m/z, calculated for $C_{15}H_{23}N_5OS$ [MH$^+$] 322.44, observed 322.

Example 3

Wafer Substrate Preparation

Prime Grade 300 mm Silicon Wafers, p-type Boron, (1 0 0) Orientation, 1-5 Ohmcm$^{-1}$ and 725 μm thickness were obtained from Process Specialties. The wafers were deposited with 1000 Å thermal oxide by dry oxidation at 1000° Celsius in a furnace under pure oxygen atmosphere for 2 hours. Commercial photoresist P5107 is spin coated on the wafers at 2000 rpm for 40 seconds using the Sokudo RF3S Coat/Develop Track (FIG. 1A). The wafers were exposed with an inverse zero layer mask using the Nikon NSR 5205 KrF Scanner (248 nm wavelength). This is followed by post exposure bake at 110° Celsius for 90 seconds and then developed using the commercially available developer NMD-3 at 2.38% (from Tokyo Ohka Kogyo America).

Oxide etching was performed by wet oxide etch of the wafers using buffered hydrofluoric acid which was prepared by mixing 5 parts of 40 weight % of ammonium fluoride (from Sigma) with 1 part of 49 weight % of hydrofluoric acid (from Sigma) for 1 minute. This is followed by stripping the wafers with Nanostrip (from CyanTek) for 24 hours. Wafers were finally washed with DI Water and sonicated in DI Water for 10 minutes. This results in the completion of substrate preparation in which the feature area has height of 1000 Å and contains thermal oxide while the non-feature area contains silicon.

Figure 1C:
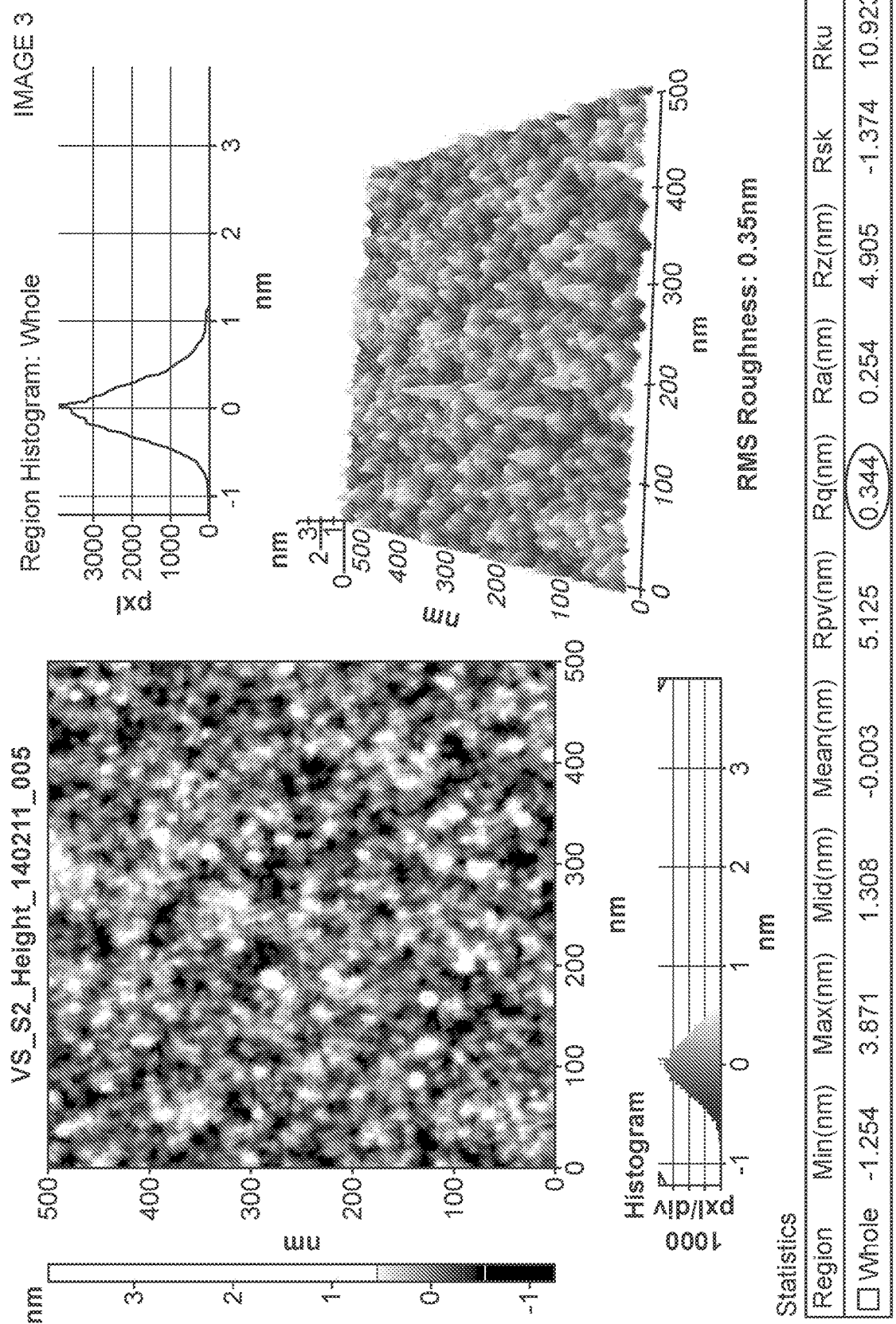

A DI 5000 AFM system was used to measure the roughness and calculate the density of the substrate. FIG. 1B shows the pillars formed after the process described in FIG. 1A. FIG. 1C shows the RMS roughness of the substrate. The density of the substrate was calculated to be approximately 100-150 pM.

Example 4

Wafer Surface Derivatization

Wafers were copiously washed with DI Water for 5 minutes and spin coated with a solution containing 1.25% (v/v) of 3-aminopropyltriethoxysilane (APTES, from Sigma Aldrich) in N-methyl-pyrollidone (NMP, from BDH Chemicals) and left at room temperature for 15 minutes. Curing of the wafers was done at 120° C. for 60 minutes under N2 atmosphere. Wafers were then spin coated with a coupling solution containing 2 weight % of Fmoc-Gly-OH (from Anaspec), 2 weight % of HOBt (from Anaspec) and 2 weight % of N,N'-diisopropylcarbodiimide (DIC, from Sigma Aldrich) in NMP and baked at 60° C. for 5 minutes. This enables coupling of Fmoc-Glycine to the free amine present in APTES. Wafers were then rinsed with NMP and then capped with 50% (v/v) of acetic anhydride mixed with 50% of NMP to cap any remaining free amines, which have not been coupled. Wafers were stripped with acetone (from BDH Chemicals) and isopropyl alcohol (IPA, from BDH Chemicals). Fmoc protection of Glycine is removed by spin coating the wafer with 5% (v/v) of piperidine (from Sigma Aldrich) in NMP and baking at 80° C. for 300 seconds. The linker Fmoc-(PEG)$_4$-COOH (from Anaspec) is then coupled to the wafer surface by spin coating a coupling solution containing 2 weight % of the linker, 2 weight % of HOBt (from Anaspec) and 2 weight % of DIC in NMP and baked at 90° C. for 120 seconds. Wafers were rinsed with NMP and then capped with 50% (v/v) of acetic anhydride mixed with 50% of NMP to cap any remaining free amines. Wafers were stripped with acetone and IPA to complete the surface derivatization process.

Example 5

Production of a NH$_2$ Coated Substrate

Wafer with an NH$_2$ surface was prepared as follows: 3-aminopropyl-triethoxy-silane (APTES) was obtained from Sigma Aldrich. 100% Ethanol was obtained from VWR International. The wafers were first washed with ethanol for 5 minutes and then in 1% by weight APTES/ethanol for 20-30 minutes to grow the silane layer. Then the wafers were cured in a 110° Celsius nitrogen bake oven to grow a mono silane layer with a —NH$_2$ group to attach a linker molecule.

Example 6

Amino Acid Activation Solution

One weight % of polymethyl methacrylate (PMMA, from Polysciences) is dissolved in NMP by sonication for 10 minutes. 2 weight % of Fmoc-amino acid (from Anaspec) is then added to the solution followed by addition of 2 weight % of HOBt (from Anaspec). The following Fmoc-amino acid can be used in the activation solution: Fmoc-citrulline, Fmoc-Ala-OH, Fmot-Cys(Trt)-OH, Fmoc-Asp(Otbu)-OH, Fmoc-Glu(OtBu)-OH, Fmoc-Phe-OH, Fmoc-Gly-OH, Fmoc-His(Trt)-OH, Fmoc-Ile-OH, Fmoc-Lys(Boc)-OH, Fmoc-Leu-OH, Fmoc-Met-OH, Fmoc-Asn(Trt)-OH, Fmoc-Pro-OH, Fmoc-Gln(Trt)-OH, Fmoc-Arg(Pbf)-OH, Fmoc-Ser(tbu)-OH, Fmoc-Thr(tbu)-OH, Fmoc-Val-OH, Fmoc-Trp(Boc)-OH, and Fmoc-Try(tbu)-OH. Finally, 1 weight % of tetrazole thione is added to the cocktail. The amino acid activation solution is then filtered using 0.05 μm filtration setup.

Example 7

Peptide Array Synthesis

A one-step amine side-chain peptide synthesis is illustrated in FIG. 2 as follows: A base resist solution containing 1 weight % of polymer and 3 weight % of piperidine dissolved in NMP is spin coated onto the wafer at 3000 rpm for 30 seconds and soft baked at 65° Celsius for 1 minute in a hot plate. Now the wafer is baked at 80° Celsius for 300 seconds. Fmoc protection is removed in all features leaving the unprotected amine group. The incoming amino acid activation solution solution is spin coated onto a wafer at 3000 rpm for 30 seconds and soft baked at 65° Celsius for 1 minute in a hot plate. Subsequently, the wafer is exposed using a reticle, which exposes desired features for which the incoming amino acid needs to be coupled at an exposure dose of 120 mJ/cm$^2$ and then hard baked at 85° Celsius for 90 seconds in a hot plate. Tetrazole thione upon exposure releases a carbodiimide and selective activation of amino acid is achieved in the exposed features. The incoming Fmoc-amino acid present in the cocktail is activated and coupled to the unprotected amine present on the wafer in the same step completing the coupling of one layer of amino acid. Each layer of coupling comprises of reticles for each incoming Fmoc-amino acid to be coupled, which exposes features independent of the rest of the reticles used for the same layer. After the completion of all amino acids for a particular layer, the wafer is then spin coated with a solution of 50 weight % of NMP and 50 weight % of acetic anhydride to cap any remaining unprotected amine remaining in any part of the wafer which have been not been coupled with the next amino acid in the layer. Wafer is stripped in acetone and IPA to remove any resist present on the surface after each step. The whole process is repeated for each individual layer of amino acid designed to be coupled to complete the synthesis of a peptide.

Example 8

Side Chain Protection Removal

After the completion of peptide synthesis, the side group protection present for some amino acids need to be removed to enable biological activity of the peptide. Side chain protection removal cocktail is prepared by mixing 95 weight % trifluoroacetic acid (TFA) (from Sigma Aldrich) and 5 weight % DI Water. Wafers are reacted with side chain protection removal cocktail for 90 mins. This is followed by washing the chips successively with TFA for 5 mins, IPA for 5 mins, and NMP for 5 mins, neutralized with 5 weight % of DIEA (from Alfa Aesar) in NMP for 5 mins, and followed by washing the wafer successively with NMP for 5 mins and IPA for 5 mins.

Example 9

Inline QC Thickness Monitoring

During the peptide array synthesis process, inline quality control is performed by testing the wafer thickness after each coating step. After coating the wafer with amino acid activation resist, the thickness of the wafer is measured using Prometrix SpectraMap (from KLA Tencor) and monitored for each step with predetermined specifications for each individual amino acid activation solution. If the thickness measured does not match with the specifications, further processing of the wafer is paused and is stripped and recoated.

Example 10

Fluorescein Quality Control

Figure 3A:
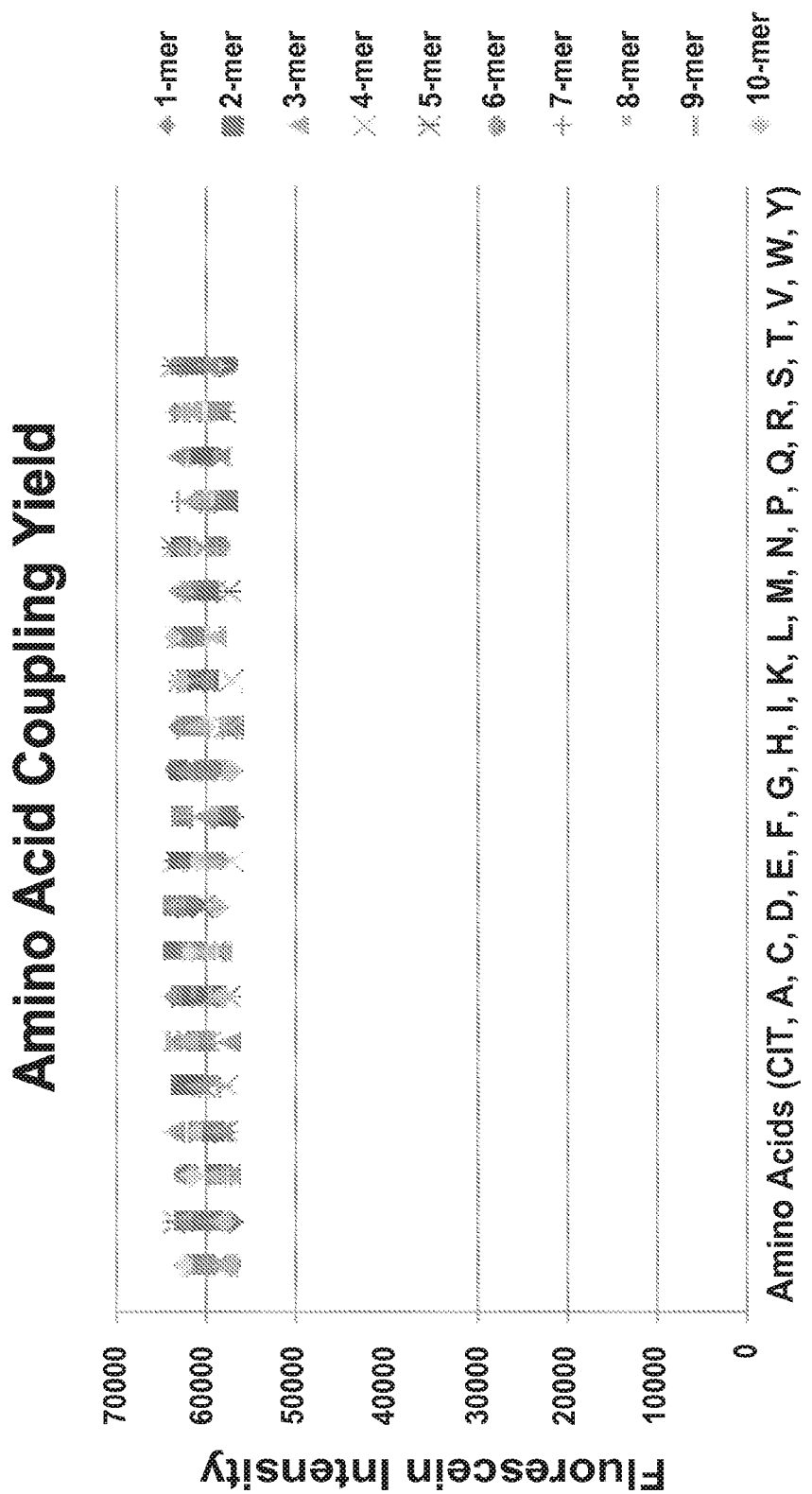
FIG. 3A-3B illustrate end-of-line fluorescein quality control of amino acid sequences synthesized on a peptide array, according to some embodiments.
Figure 3B:
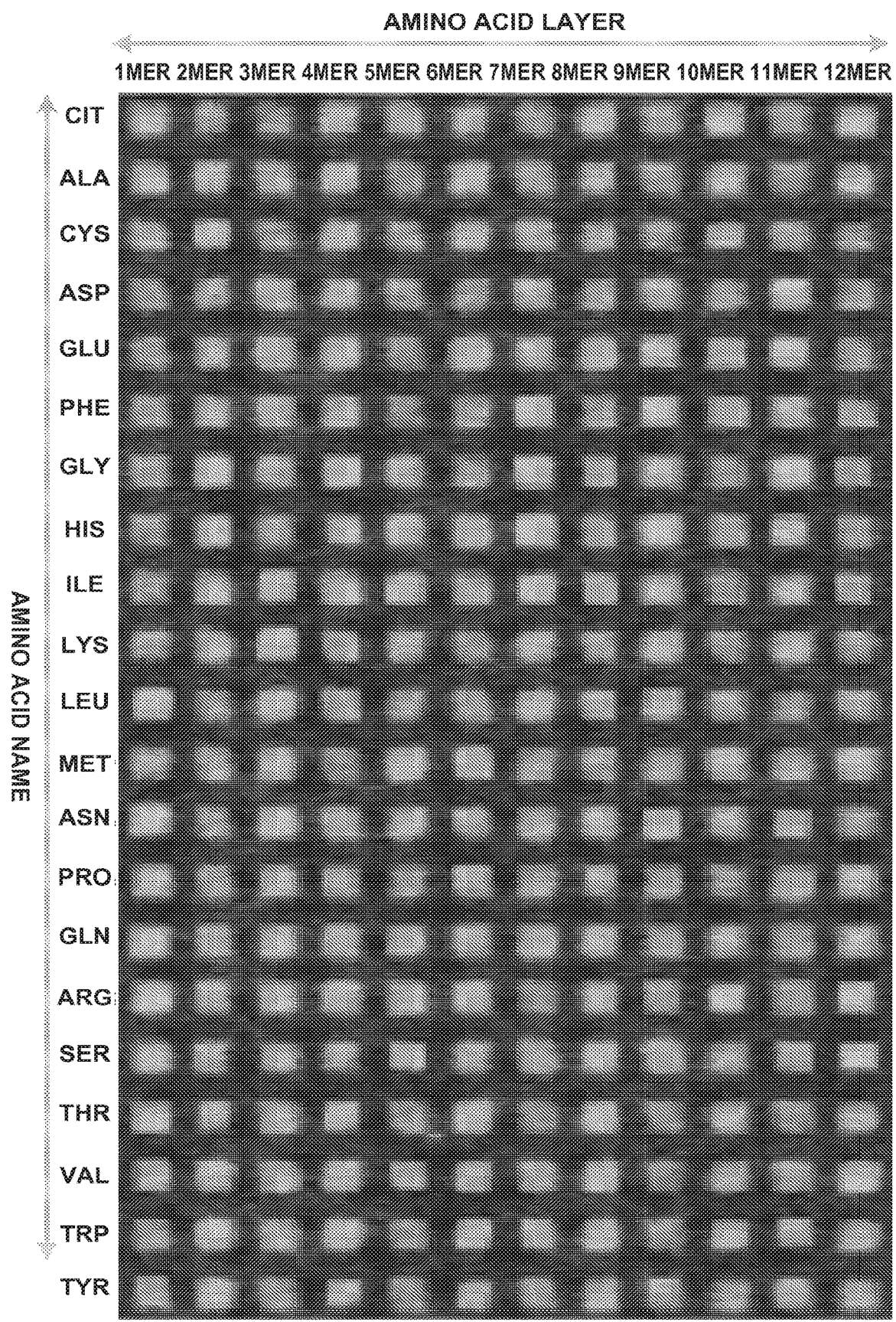
Figure 4A:
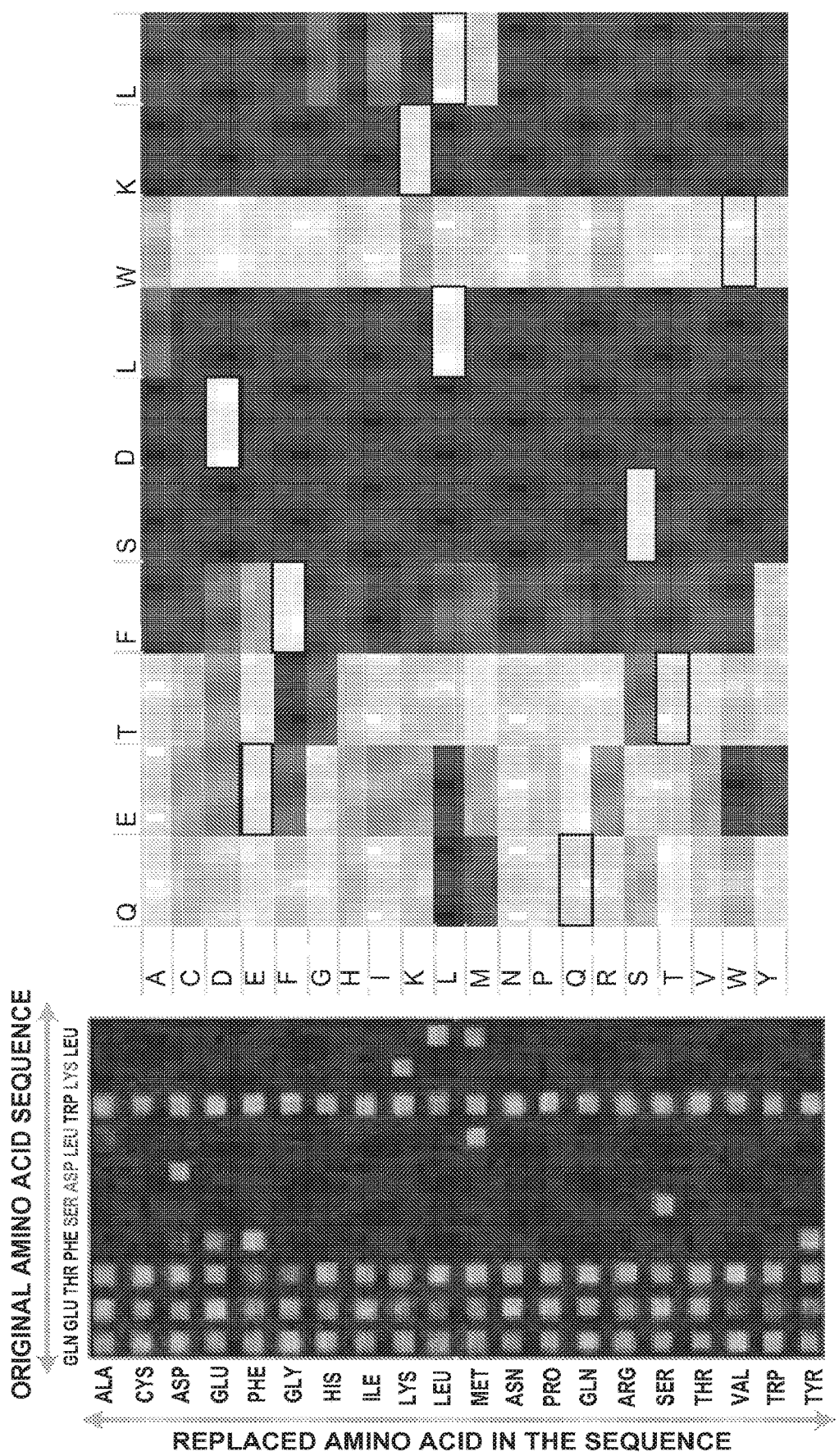
FIG. 4A-4F illustrate end-of-line biological quality control of amino acid sequences synthesized on a peptide array using monoclonal antibodies, according to some embodiments.
Figure 4B:
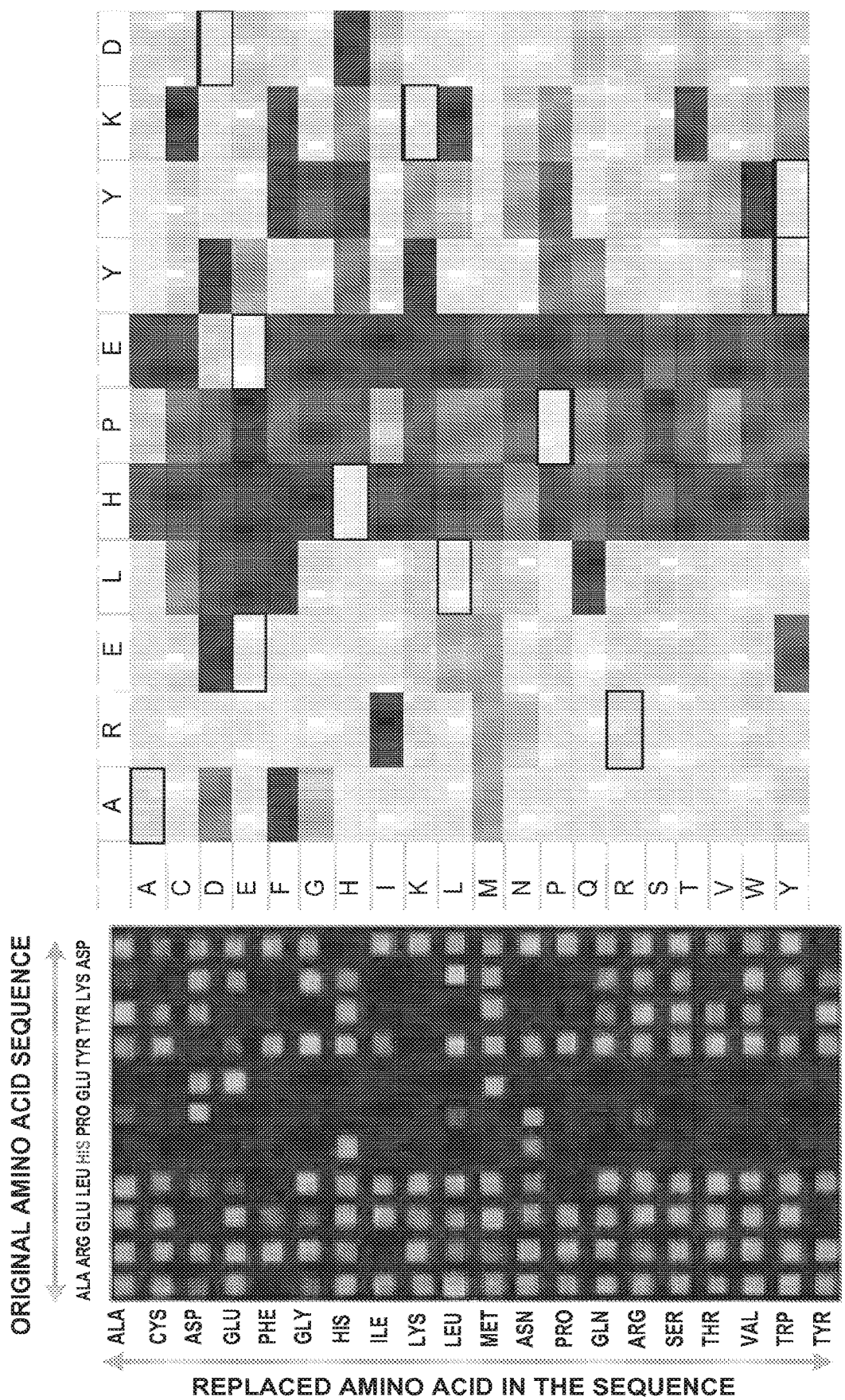
Figure 4C:
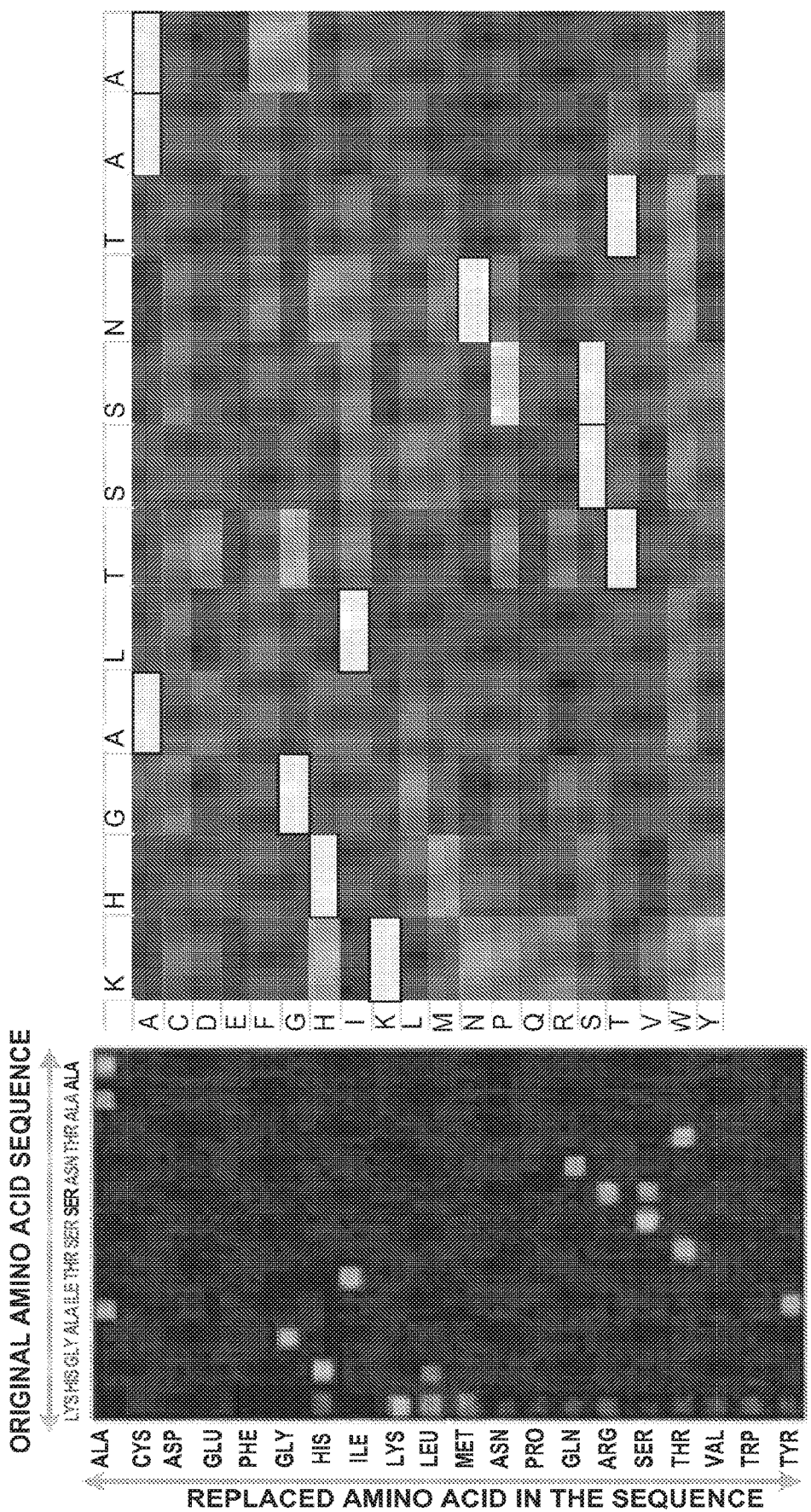
Figure 4D:
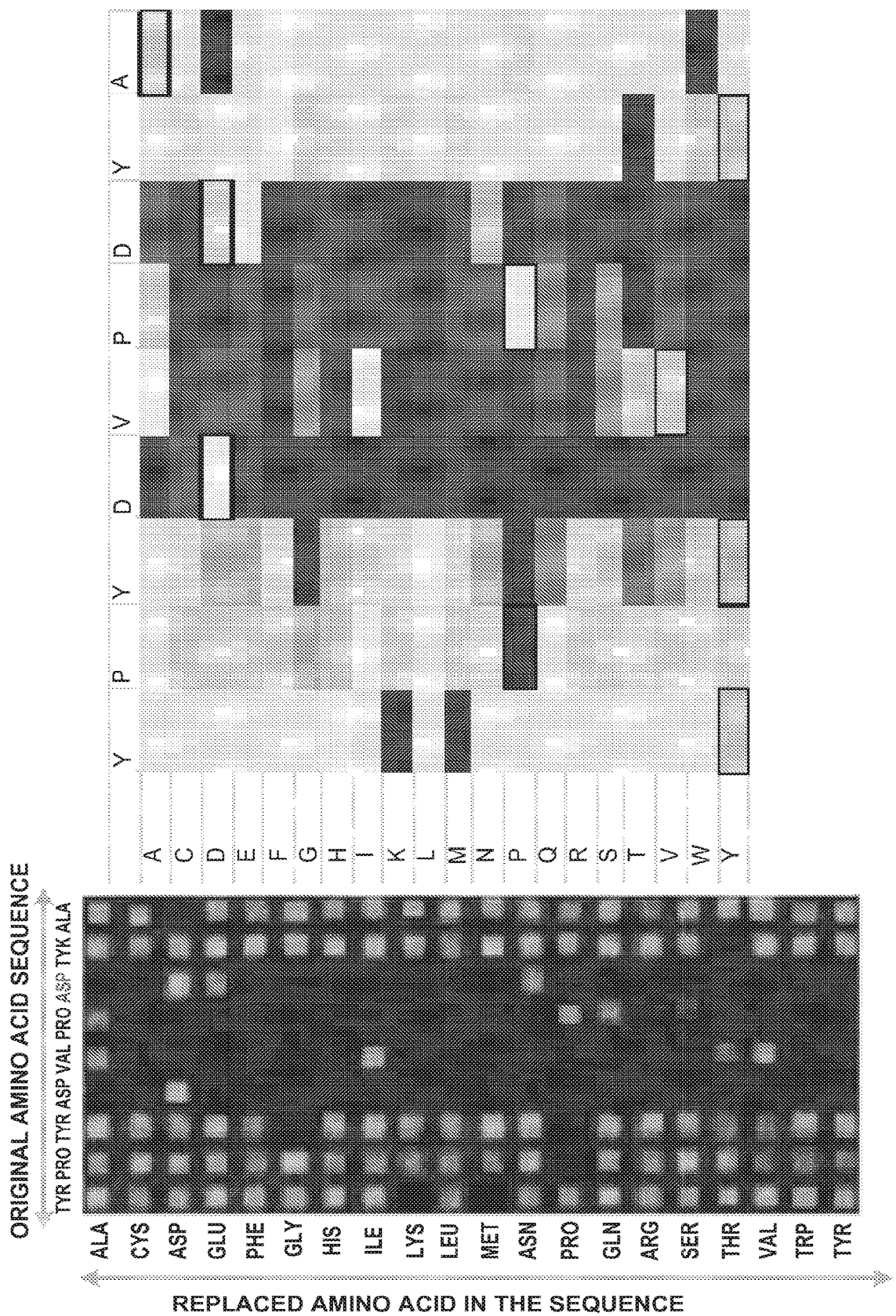
Figure 4E:
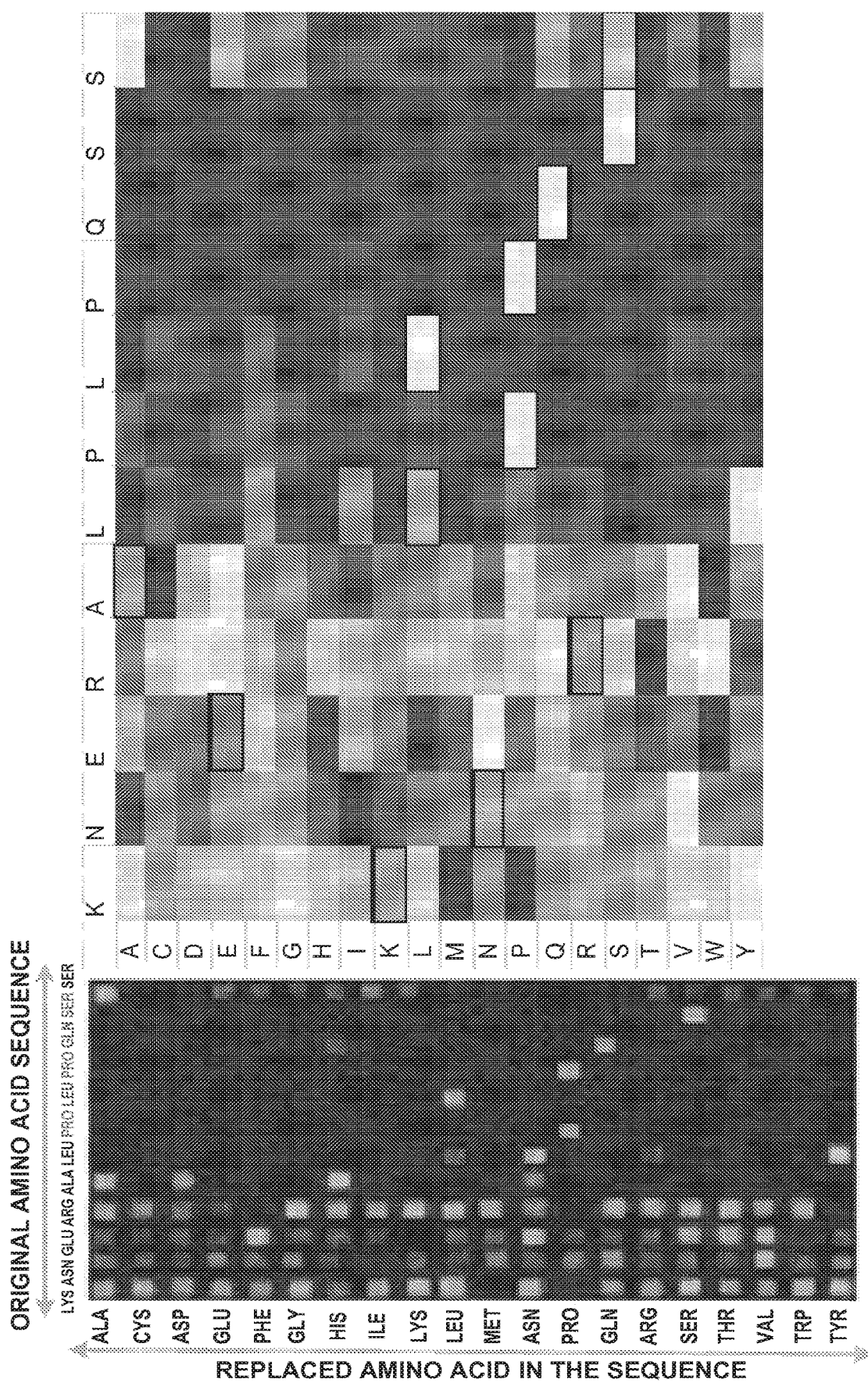
Figure 4F:
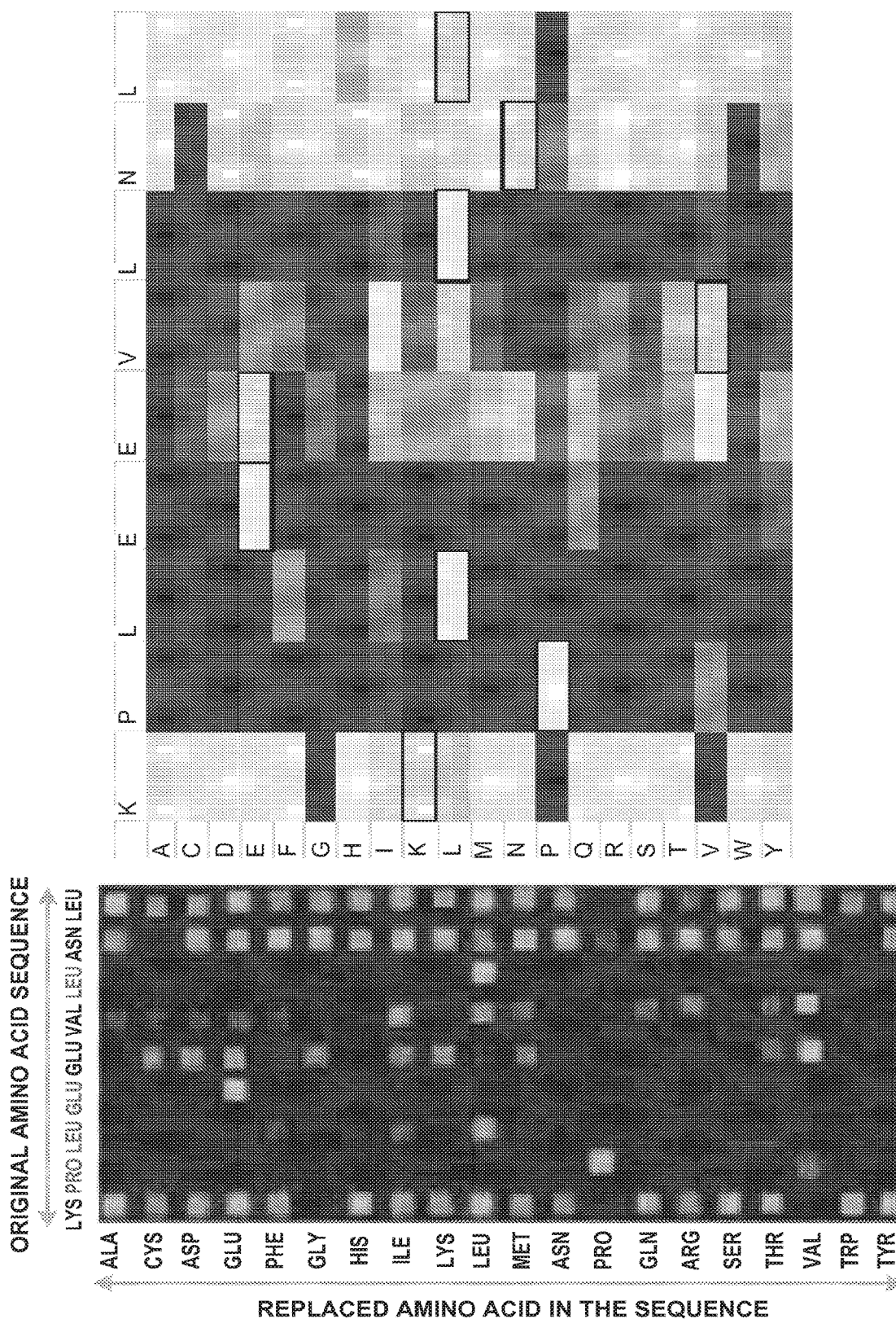

After the synthesis process is completed, end-of-line fluorescein quality control is performed. The final amino acid in each peptide sequence was deprotected by base (10% (v/v) of piperidine in NMP) for 20 mins and was coupled to a solution containing 1 weight % 5(6)-carboxyfluorescein (5(6)-FAM, from Anaspec), 2 weight % of DIC and 2 weight % of HOBt dissolved in NMP for 30 mins. This was followed by washing steps successively with NMP for 5 mins, ethanol for 5 mins, mixture of 50 weight % EDA (from Sigma Aldrich) and 50 weight % of ethanol for 30 mins, and ethanol for 15 mins and IPA for 5 mins. This process was used to analyze the individual coupling yield of each amino acid coupled in each step in addition to the step yield of each peptide sequence coupled. Sample data is shown in FIGS. 3A and 3B.

Example 11

Biological Quality Control

After the synthesis process was completed, end-of-line biological quality control was performed. Monoclonal antibodies to known peptide sequences were obtained from Abcam. Each amino acid in the peptide sequence was replaced one at a time to determine the key amino acid/ amino acids needed for the antibody to recognize the sequence. For example, in the sequence Leu-Lys-Trp-Leu-Asp-Ser-Phe-Thr-Glu-Gln (LKWLDSFTEQ), Leu was replaced one at a time by Cit, Ala, Cys, Asp, Glu, Phe, Gly, His, Ile, Lys, Met, Asn, Pro, Gln, Arg, Ser, Thr, Val, and Tyr, and similarly other amino acids in the sequence were replaced one at a time. All sequences were designed and grown on the wafer and all sequences were tested for biological activity using the monoclonal antibody obtained for the given sequence. For a particular sequence, an amino acid was considered to be a key amino acid when the biological activity of the sequence is high when amino acid was present and was low when the key amino acid was replaced by any of the remaining amino acids. Sample data obtained is shown in FIG. 4A-4F. From the heat map shown in FIG. 4A, it was determined that the important amino acids in this sequence are LKWLDSFTEQ with the key amino acids underlined and in bold face. If any other amino acids were used in place of the key amino acid, the sequence did not display any biological activity. Thus, an amino acid was correlated with a particular sequence, for which it is a key amino acid. When the amino acid was grown in each layer, the correlated sequence was also grown in the design to check the coupling yield of the amino acid using the biological performance characteristic. Similarly, for FIG. 4B-4F, key amino acids were determined and included in every layer as part of the Bio quality control test for each layer amino acid. For FIG. 4B-4F the sequences were DKYYEPHLERA, AATNSSTIAGHK, AYDPVDYPY, S SQPLPLARENK, LNLVEELPK, respectively, with the key amino acids underlined and in bold face.

Example 12

Production of a Substrate with Pillars

This example describes how to construct a substrate comprising pillars. Silicon wafers with 2.4 μm thermally grown oxide were obtained from University Wafers. The surface of the silicon wafer was cleaned with deionized water to remove contaminants from the wafer surface. The surface of the silicon wafer was primed for chemical adhesion of an organic compound to the wafer by applying vapors of hexamethyldisilizane (HMDS) onto a heated wafer substrate using a spray module at 200-220° Celsius for 30-50 seconds. HMDS was obtained from Sigma Aldrich Inc. HMDS acts as a "bridge" with properties to bind to both the wafer surface and the photoresist. The wafers were spun coat in a photoresist coat module with a commercially available deep Ultra violet photoresist, P5107 obtained from Rohm and Haas or AZ DX7260p 700 from AZ Electronic Materials, to obtain a thickness of 6000 Å. The wafers were then baked in a hot plate at 120° Celsius for 60 seconds.

Photomasks that have the patterned regions to create the features were used to image the array on to the substrate surface. The wafers were then exposed in a 248 nm deep ultra violet radiation scanner tool, Nikon 5203, with expose energy of 18 mJ/cm$^2$. The wafers were then post-exposure baked at 110° Celsius for 120 seconds in a hot plate and developed with commercially available NMD-3 developer, obtained from Tokyo Ohka Kogyo Co., Ltd., for 60 seconds.

After this the oxide was etched by using either a wet etch process or dry plasma etch process. Standard semiconductor etch techniques were used. Oxide etch depths were from 1000 Å to 2000 Å.

After etching, the resist was lifted off with the following process: The wafers were left in Nanostrip obtained from Cyantek Inc. overnight and then dipped in Piranha solution for 90 min. Piranha solution is a 50:50 mixture of sulfuric acid and hydrogen peroxide. Sulfuric acid and hydrogen peroxide were obtained from Sigma Aldrich Corp. Plasma ashing was performed to oxidize the remaining impurities. This process produced a substrate having pillars of silicon dioxide.

Derivatization: The wafers were then surface derivatized using the methods provided in Examples 4 and 5 to coat the pillar surface with free amine attachment groups (i.e., $NH_2$ groups).

---

What is claimed is:

1. A method of attaching a coupling molecule to a substrate, comprising:
   obtaining a substrate comprising a plurality of amine groups for linking to a coupling molecule;
   contacting said substrate with a carboxylic acid activating formulation comprising: a carboxylic acid activating compound, wherein said compound is 1-(3-(diethylamino)-propyl)-4-(2-methoxyphenyl)-1,4-dihydro-5H-tetrazole-5-thione, a coupling molecule, and a solvent;
   selectively exposing said photoactive coupling formulation to light, thereby activating a carboxylic group of said coupling molecule at a selectively exposed area;
   coupling the activated carboxylic group of said coupling molecule to at least one of said plurality of amine groups at said selectively exposed area, wherein said coupling is performed multiple times at different selectively exposed areas on said substrate and wherein said coupling step has a coupling efficiency of at least 98.5%; and
   optionally repeating said method to produce a desired polymer at said at least one carboxylic acid group.

2. The method of claim 1, wherein said coupling molecule is an amino acid.

3. The method of claim 2, wherein said amino acid has a protecting group attached to an amine group.

4. The method of claim 3, wherein said protecting group is Fmoc.

5. A method of attaching a coupling molecule to a substrate, comprising:
   obtaining a substrate comprising a plurality of amine groups for linking to a coupling molecule;
   contacting said substrate with a carboxylic acid activating formulation comprising: a carboxylic acid activating compound, wherein said compound is 1-(3-(diethylamino)-propyl)-4-(2-methoxyphenyl)-1,4-dihydro-5H-tetrazole-5-thione, a coupling molecule, and a solvent;
   selectively exposing said photoactive coupling formulation to light, thereby activating a carboxylic group of said coupling molecule at a selectively exposed area;
   coupling the activated carboxylic group of said coupling molecule to at least one of said plurality of amine groups at said selectively exposed area, wherein said coupling is performed multiple times at different selectively exposed areas on said substrate and wherein said coupling step has a coupling efficiency of at least 90%; and
   optionally repeating said method to produce a desired polymer at said at least one carboxylic acid group.

6. The method of claim 5, wherein said coupling molecule is an amino acid.

7. The method of claim 6, wherein said amino acid has a protecting group attached to an amine group.

8. The method of claim 7, wherein said protecting group is Fmoc.

9. A method of attaching a coupling molecule to a substrate, comprising:
   obtaining a substrate comprising a plurality of amine groups for linking to a coupling molecule;
   contacting said substrate with a carboxylic acid activating formulation comprising: a carboxylic acid activating compound, wherein said compound is 1-(3-(diethylamino)-propyl)-4-(2-methoxyphenyl)-1,4-dihydro-5H-tetrazole-5-thione, a coupling molecule comprising an amino acid with an Fmoc protecting group attached to an amine group, and a solvent;
   selectively exposing said photoactive coupling formulation to light, thereby activating a carboxylic group of said coupling molecule at a selectively exposed area;
   coupling the activated carboxylic group of said coupling molecule to at least one of said plurality of amine groups at said selectively exposed area; and optionally repeating said method to produce a desired polymer at said at least one carboxylic acid group.

10. The method of claim 9, wherein said coupling step has a coupling efficiency of at least 98.5%.

11. The method of claim 9, wherein said coupling step has a coupling efficiency of at least 90%.

12. A method of attaching a coupling molecule to a substrate, comprising:
   obtaining a substrate comprising a plurality of amine groups for linking to a coupling molecule;
   contacting said substrate with a carboxylic acid activating formulation comprising: a carboxylic acid activating compound, wherein said compound is 1-(3-(diethyl-amino)-propyl)-4-(2-methoxyphenyl)-1,4-dihydro-5H-tetrazole-5-thione, a coupling molecule comprising an amino acid with an Fmoc protecting group attached to an amine group, and a solvent;
   selectively exposing said photoactive coupling formulation to light, thereby activating a carboxylic group of said coupling molecule at a selectively exposed area;
   coupling the activated carboxylic group of said coupling molecule to at least one of said plurality of amine groups at said selectively exposed area, wherein said coupling is performed multiple times at different selectively exposed areas on said substrate and wherein said coupling step has a coupling efficiency of at least 90%; and
   optionally repeating said method to produce a desired polymer at said at least one carboxylic acid group.

13. The method of claim 12, wherein said coupling step has a coupling efficiency of at least 98.5%.

14. A method of attaching a coupling molecule to a substrate, comprising:
   obtaining a substrate comprising a plurality of amine groups for linking to a coupling molecule;
   contacting said substrate with a carboxylic acid activating formulation comprising: a carboxylic acid activating compound, wherein said compound is 1-(3-(diethyl-amino)-propyl)-4-(2-methoxyphenyl)-1,4-dihydro-5H-tetrazole-5-thione, a coupling molecule comprising an amino acid with an Fmoc protecting group attached to an amine group, and a solvent;
   selectively exposing said photoactive coupling formulation to light, thereby activating a carboxylic group of said coupling molecule at a selectively exposed area;
   coupling the activated carboxylic group of said coupling molecule to at least one of said plurality of amine groups at said selectively exposed area, wherein said coupling is performed multiple times at different selectively exposed areas on said substrate and wherein said coupling step has a coupling efficiency of at least 98.5%; and
   optionally repeating said method to produce a desired polymer at said at least one carboxylic acid group.

* * * * *

SEQUENCE LISTING

```
<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Lys Trp Leu Asp Ser Phe Thr Glu Gln
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Lys Tyr Tyr Glu Pro His Leu Glu Arg Ala
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ala Thr Asn Ser Ser Thr Ile Ala Gly His Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Tyr Asp Pro Val Asp Tyr Pro Tyr
1               5
```

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ser Gln Pro Leu Pro Leu Ala Arg Glu Asn Lys
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Asn Leu Val Glu Glu Leu Pro Lys
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Glu Thr Phe Ser Asp Leu Trp Lys Leu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Arg Glu Leu His Pro Glu Tyr Tyr Lys Asp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys His Gly Ala Ile Thr Ser Ser Asn Thr Ala Ala
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 10

Tyr Pro Tyr Asp Val Pro Asp Tyr Ala
1               5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Asn Glu Arg Ala Leu Pro Leu Pro Gln Ser Ser
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Pro Leu Glu Glu Val Leu Asn Leu
1               5
```